US010428311B2

(12) United States Patent
Sekiguchi et al.

(10) Patent No.: US 10,428,311 B2
(45) Date of Patent: *Oct. 1, 2019

(54) METHOD FOR ENHANCING ACTIVITY OF LAMININ FRAGMENTS AS CELL CULTURE MATRIX

(71) Applicant: OSAKA UNIVERSITY, Osaka (JP)

(72) Inventors: Kiyotoshi Sekiguchi, Osaka (JP); Ko Tsutsui, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/325,743

(22) PCT Filed: Jul. 15, 2015

(86) PCT No.: PCT/JP2015/070298
§ 371 (c)(1),
(2) Date: Feb. 9, 2017

(87) PCT Pub. No.: WO2016/010082
PCT Pub. Date: Jan. 21, 2016

(65) Prior Publication Data
US 2017/0159020 A1    Jun. 8, 2017

(30) Foreign Application Priority Data

Jul. 16, 2014  (JP) ................................ 2014-145536

(51) Int. Cl.
*C12N 5/074* (2010.01)
*C12N 15/00* (2006.01)
*C12N 15/09* (2006.01)

(52) U.S. Cl.
CPC ........... *C12N 5/0696* (2013.01); *C12N 15/00* (2013.01); *C12N 15/09* (2013.01); *C12N 2533/52* (2013.01)

(58) Field of Classification Search
CPC ...... C12N 5/0696; C12N 15/00; C12N 15/09; C12N 2533/52
USPC ....................................................... 435/375
See application file for complete search history.

(56) References Cited

U.S. PATENT DOCUMENTS

| 5,932,473 A | 8/1999 | Swiderek et al. |
| 2007/0269886 A1 | 11/2007 | Qian et al. |
| 2012/0220031 A1 | 8/2012 | Sekiguchi et al. |
| 2012/0282691 A1 | 11/2012 | Qian et al. |
| 2014/0127806 A1 | 5/2014 | Sekiguchi et al. |
| 2016/0052994 A1 | 2/2016 | Sekiguchi et al. |
| 2016/0137965 A1 | 5/2016 | Sekiguchi et al. |

FOREIGN PATENT DOCUMENTS

| JP | 6-98757 | 4/1994 |
| JP | 11-164685 | 6/1999 |
| JP | 2007-306922 | 11/2007 |
| WO | 2011/043405 | 4/2011 |
| WO | 2012/137970 | 10/2012 |
| WO | 2013/047763 | 4/2013 |
| WO | WO 2013/047763 | * 4/2013 |
| WO | 2014/103534 | 7/2014 |
| WO | 2014/199754 | 12/2014 |

OTHER PUBLICATIONS

Extended European Search Report dated Nov. 17, 2017 in corresponding European patent application No. 15821563.2.
Alan Tin-Lun Lam et al., "Cationic Surface Charge Combined with Either Vitronection or Laminin Dictates the Evolution of Human Embryonic Stem Cells/Microcarrier Aggregates and Cell Growth in Agitated Cultures", Stem Cells and Development, vol. 23, No. 14, Jul. 15, 2014, pp. 1688-1703.
Sanna Vuoristo et al., "A Novel Feeder-Free Culture System for Human Pluripotent Stem Cell Culture and Induced Pluripotent Stem Cell Derivation", PLOS ONE, vol. 8, No. 10, Oct. 2, 2013, pp. e76205.
Jack W. Lambshed et al., "Defining synthetic surfaces for human pluripotent stem cell culture", Cell Regeneration, Biomed Central Ltd, London, UK, vol. 2, No. 1, Nov. 22, 2013, p. 7.
International Search Report dated Oct. 13, 2015 in International Application No. PCT/JP2015/070298.
Nakagawa, M et al., "A novel efficient feeder-free culture system for the derivation of human induced pluripotent stem cells", Scientific Reports, Jan. 8, 2014, vol. 4, No. 3594, pp. 1-7.
Miyazaki, T et al., "Laminin E8 fragments support efficient adhesion and expansion of dissociated human pluripotent stem cells", Nature Communications, Dec. 4, 2012, pp. 1-11.
International Preliminary Report on Patentability dated Jan. 19, 2017 in International Application No. PCT/JP2015/070298.

* cited by examiner

*Primary Examiner* — Jennifer M. H. Tichy
(74) *Attorney, Agent, or Firm* — Wenderoth, Lind & Ponack, L.L.P.

(57) ABSTRACT

The present invention provides a novel technique in a cell culture method using a cell culture vessel coated with a laminin fragment, which novel technique achieves cell culture as in the case of using a recommended coating concentration even when the coating concentration is lower than the recommended coating concentration. The present invention relates to a method for enhancing an activity for mammalian cultured cells of a laminin fragment or a variant thereof each having integrin binding activity.

6 Claims, 16 Drawing Sheets
Specification includes a Sequence Listing.

| 521E8 (μg/cm²) | 0.25 | 01.25 | 0.125 | 0.125 | 0.125 |
|---|---|---|---|---|---|
| Addition | None | None | None | HSA (500 μg/mL) | HSA (2000 μg/mL) |
| Storage period (week) | 0 week (fresh) | 0 week (fresh) | 13 weeks | 13 weeks | 13 weeks |

Fig. 10

| 511E8 (μg/cm²) | 0.5 | 0.25 | 0.25 | 0.25 | 0.25 |
|---|---|---|---|---|---|
| Addition | None | None | None | Gelatin (500 μg/mL) | Gelatin (2000 μg/mL) |
| Storage period (month) | 0 month (fresh) | 0 month (fresh) | 12 months | 12 months | 12 months |

| 521E8 (μg/cm²) | 0.25 | 0.125 | 0.125 | 0.125 | 0.125 |
|---|---|---|---|---|---|
| Addition | None | None | None | HSA (500 μg/mL) | HSA (2000 μg/mL) |
| Storage period (month) | 0 month (fresh) | 0 month (fresh) | 12 months | 12 months | 12 months |

METHOD FOR ENHANCING ACTIVITY OF LAMININ FRAGMENTS AS CELL CULTURE MATRIX

TECHNICAL FIELD

The present invention relates to a method for enhancing an activity of a laminin fragment or a variant thereof for mammalian cultured cells, a method for culturing mammalian cells using a cell culture vessel coated with the laminin fragment or a variant thereof of which the activity is enhanced, and a coating solution usable for these methods.

BACKGROUND ART

Human pluripotent stem cells, such as human ES cells and human iPS cells, are receiving worldwide attention for their potential application to regenerative medicine. The requirement for the application of human pluripotent stem cells to regenerative medicine is to develop culture techniques for culturing and propagating such stem cells in a safe and stable manner. In particular, a pressing issue is the development of a method for stably culturing such stem cells under conditions in which no feeder cells are used (feeder-free) and no xenogeneic components are contained in the culture system (xeno-free).

Various culture matrices which enable cell culture under feeder-free and xeno-free conditions have so far been developed, and are exemplified by vitronectin, laminin α5β1γ1 (hereinafter referred to as "laminin 511"), laminin α5β2γ1 (hereinafter referred to as "laminin 521"), etc. In particular, a recombinant laminin 511E8 fragment (hereinafter referred to as "laminin 511E8"), which contains only the integrin binding site of laminin 511, was shown by the present inventors to have very strong adhesive activity for human pluripotent stem cells and be superior to any other culture matrix developed so far (see Patent Literature 1 and Non Patent Literature 1). With the use of laminin 511E8 as a culture matrix, all the culture steps including establishment, expansion culture and directed differentiation of human iPS cells can be consistently carried out under feeder-free conditions (Non Patent Literature 2).

For cell culture using laminin 511E8 as a matrix, the culture surface of a culture vessel needs coating with laminin 511E8. However, since laminin 511E8 and many other culture matrices which enable cell culture under feeder-free conditions are prepared by gene recombination techniques, the cost for preparing such recombinant proteins used for coating culture vessels is heavy economic burden in human pluripotent stem cell culture. The coating concentration of laminin 511E8 used for culture of human ES cells or human iPS cells is usually 0.25 µg/cm² to 1.0 µg/cm², which corresponds to 2.4 µg to 9.6 µg of laminin 511E8 per dish in the case of coating a standard 35-mm-diameter culture dish (usable surface area: 9.6 cm²), for example. Laminin 511E8 is a heterotrimer consisting of C-terminal regions of laminin α5, β1 and γ1 chains and contains many disulfide bonds in the molecule. Due to the disulfide bonds, a recombinant laminin 511E8 is difficult to produce using prokaryotic (e.g., E. coli) expression systems, and therefore, the use of animal or insect cell expression systems, albeit costly, is necessary for the production of a recombinant laminin 511E8. For popularization of the use of laminin 511E8 as a feeder-free culture matrix for human pluripotent stem cells, the production cost of laminin 511E8 needs to be reduced by improvement of the production method, and furthermore, the coating concentration of laminin 511E8 suitable for human pluripotent stem cell culture needs to be reduced by enhancement of the activity of laminin 511E8. For the success of such attempts to curb the cost for coating culture vessels, the development of a novel technique for enhancing the activity of laminin 511E8 is strongly required.

In addition, in order to popularize the culture method using laminin 511E8 domestically and abroad, there is need for the development of products which enable even an unskilled person to easily accomplish a coating operation with little variation in the coating concentration. Currently, a freeze-dried product of laminin 511E8 for coating culture vessels is commercially available (trade name: iMatrix-511, manufactured by Nippi, Inc.). In a usual procedure for use as a culture matrix, this freeze-dried laminin 511E8 product is dissolved at a concentration of 200 to 1000 µg/mL to prepare a laminin 511E8 stock solution, and this stock solution is aliquoted and kept frozen until use. For coating a culture vessel, the frozen laminin 511E8 stock solution is thawed and diluted to a desired coating concentration in PBS or the like, and the diluted solution is applied on the culture surface of the culture vessel. In this procedure, there is a risk of human errors occurring at the steps of dissolution of the freeze-dried product and dilution of the stock solution, and therefore, it is difficult to completely prevent the variation in the coating concentration among separate coating operations. If a laminin 511E8 solution previously diluted to a desired coating concentration can be used in every coating operation, even an inexperienced operator will be able to carry out a stable coating operation and thus the variation in the coating concentration will be easily prevented. In addition, the steps of thawing and diluting the laminin 511E8 stock solution will not be necessary, and thus, operation time will be significantly reduced. For these reasons, there is need for the development of a laminin 511E8 solution that does not need to be prepared immediately before use and can be stably stored without loss of the activity of laminin 511E8 for a long period of time.

The prior art disclosed in Patent Literature 2 is analogous to the present invention and is a method for enhancing an activity of laminin 511 for cells in a method for cell culture under conditions in which full-length laminin 511 has been immobilized. Specifically, Patent Literature 2 discloses "a method for enhancing an activity of laminin 511 for cells, comprising culturing mammalian cells under conditions in which laminin 511 and another polypeptide and/or peptide are immobilized, the polypeptide and/or peptide being selected from the group consisting of serum; blood proteins other than extracellular matrix proteins, such as serum albumin, prealbumin, immunoglobulin, α-globulin, β-globulin, α-1-antitrypsin (α1-AT), haptoglobin (Hp), α-2-macroglobulin (α2-M), α-fetoprotein (AFP), transferrin, retinol-binding proteins (RBPs) and adiponectin; gelatin; proteins belonging to the tumor necrosis factor (TNF) family; and peptone" (claim 7). However, the invention disclosed in Patent Literature 2 is an invention relating to a full-length laminin 511, and is completely different from the present invention in that a higher concentration of the polypeptide used in combination with the full-length laminin 511 is less effective for the enhancement of the activity.

CITATION LIST

Patent Literature

Patent Literature 1: WO 2011/043405
Patent Literature 2: WO 2013/047763

Non Patent Literature

Non Patent Literature 1:
Miyazaki, T. et al., Nature Commun. 3: 1236, doi: 10.1038/ncomms2231, 2012
Non Patent Literature 2:
Nakagawa, M. et al., Scientific Reports, 4: 3594, doi: 10.1038/srep03594, 2014

SUMMARY OF INVENTION

Technical Problem

An object of the present invention is to provide a novel technique in a cell culture method using a cell culture vessel coated with a laminin fragment or a variant thereof, which novel technique achieves cell culture as in the case of using a recommended coating concentration even when the coating concentration is lower than the recommended coating concentration. Another object of the present invention is to provide a coating solution used for coating a cell culture vessel with a laminin fragment or a variant thereof, which coating solution does not need to be prepared immediately before use and can be kept refrigerated in a stable condition for a long period of time.

Solution to Problem

In order to achieve the above-mentioned object, the present invention includes the following.
[1] A method for enhancing an activity for mammalian cultured cells of a laminin fragment or a variant thereof each having integrin binding activity,
the method comprising bringing a culture surface of a cell culture vessel into contact with a coating solution containing the laminin fragment or a variant thereof and a protein that is neither a laminin nor a laminin fragment, thereby achieving coating of the culture surface with the laminin fragment or a variant thereof,
the coating solution containing the laminin fragment or a variant thereof in such an amount that the culture surface is coated at a concentration lower than 0.5 µg/cm$^2$,
the protein that is neither a laminin nor a laminin fragment being present at a concentration of 50 µg/mL or higher in the coating solution, and
the activity for mammalian cultured cells being at least one kind selected from activity for binding to cell-surface adhesion receptors, cell-adhesive activity, cell growth-supporting activity and colony formation-promoting activity.
[2] The method according to the above [1], wherein the protein that is neither a laminin nor a laminin fragment is present at a concentration of 200 µg/mL or higher in the coating solution.
[3] The method according to the above [2], wherein the protein that is neither a laminin nor a laminin fragment is present at a concentration of 500 µg/mL or higher in the coating solution.
[4] The method according to any one of the above [1] to [3], wherein the protein that is neither a laminin nor a laminin fragment has a molecular weight of 10000 or higher.
[5] The method according to the above [4], wherein the protein that is neither a laminin nor a laminin fragment is one or more kinds selected from the group consisting of gelatin, serum albumin, transferrin, myelin basic protein, β-lactoglobulin, glutathione S-transferase and collagen.
[6] The method according to any one of the above [1] to [5], wherein the laminin fragment is derived from at least one kind selected from laminin α5β1γ1, laminin α5β2γ1, laminin α4β1γ1 and laminin α2β1γ1.
[7] The method according to any one of the above [1] to [6], wherein the laminin fragment is a laminin E8 fragment.
[8] A method for culturing mammalian cells using a cell culture vessel coated with a laminin fragment or a variant thereof each having integrin binding activity,
the cell culture vessel being prepared by bringing a culture surface of the cell culture vessel into contact with a coating solution containing the laminin fragment or a variant thereof and a protein that is neither a laminin nor a laminin fragment,
the coating solution containing the laminin fragment or a variant thereof in such an amount that the culture surface is coated at a concentration lower than 0.5 µg/cm$^2$, and
the protein that is neither a laminin nor a laminin fragment being present at a concentration of 50 µg/mL or higher in the coating solution.
[9] The method according to the above [8], wherein the protein that is neither a laminin nor a laminin fragment is present at a concentration of 200 µg/mL or higher in the coating solution.
[10] The method according to the above [8] or [9], wherein the protein that is neither a laminin nor a laminin fragment has a molecular weight of 10000 or higher.
[11] The method according to any one of the above [8] to [10], wherein the laminin fragment is derived from at least one kind selected from laminin α5β1γ1, laminin α5β2γ1, laminin α4β1γ1 and laminin α2β1γ1.
[12] The method according to any one of the above [8] to [11], wherein the laminin fragment is a laminin E8 fragment.
[13] A solution for coating a culture surface of a cell culture vessel with a laminin fragment or a variant thereof,
the solution containing a laminin fragment or a variant thereof each having an integrin binding activity and a protein that is neither a laminin nor a laminin fragment,
the laminin fragment or a variant thereof being present at a concentration of 5 µg/mL or lower, and
the protein that is neither a laminin nor a laminin fragment being present at a concentration of 50 µg/mL or higher.
[14] The solution according to the above [13], wherein the laminin fragment or a variant thereof is present in an amount adjusted so that the culture surface of the cell culture vessel is coated with the laminin fragment or a variant thereof at a concentration lower than 0.5 µg/cm$^2$.
[15] The solution according to the above [13] or [14], wherein the protein that is neither a laminin nor a laminin fragment has a molecular weight of 10000 or higher.
[16] The solution according to any one of the above [13] to [15], wherein the laminin fragment is a laminin E8 fragment.

Advantageous Effects of Invention

The present invention provides a method for enhancing an activity for mammalian cultured cells of a laminin fragment or a variant thereof each having integrin binding activity. According to the activity-enhancing method of the present invention, even when the coating concentration of the laminin fragment is lower than the recommended coating concentration, cell culture can be achieved as in the case of the recommended coating concentration. The present invention also provides a coating solution containing a laminin fragment or a variant thereof for coating a cell culture vessel. The coating solution of the present invention does not need to be prepared immediately before use and can be stably stored for a long period of time. Thus, with the use of the coating solution, human errors can be avoided, and cell culture vessels can be always coated at the same concentration without much skill.

BRIEF DESCRIPTION OF DRAWINGS

FIG. 10 shows the results of alkaline phosphatase staining of human iPS cells cultured for one week on a 24-well cell culture plate coated with a coating solution of laminin 511E8 plus gelatin stored in a polypropylene tube at 4° C. for 12 months or a coating solution of laminin 511E8 prepared immediately before use.

DESCRIPTION OF EMBODIMENTS

Figure 1:
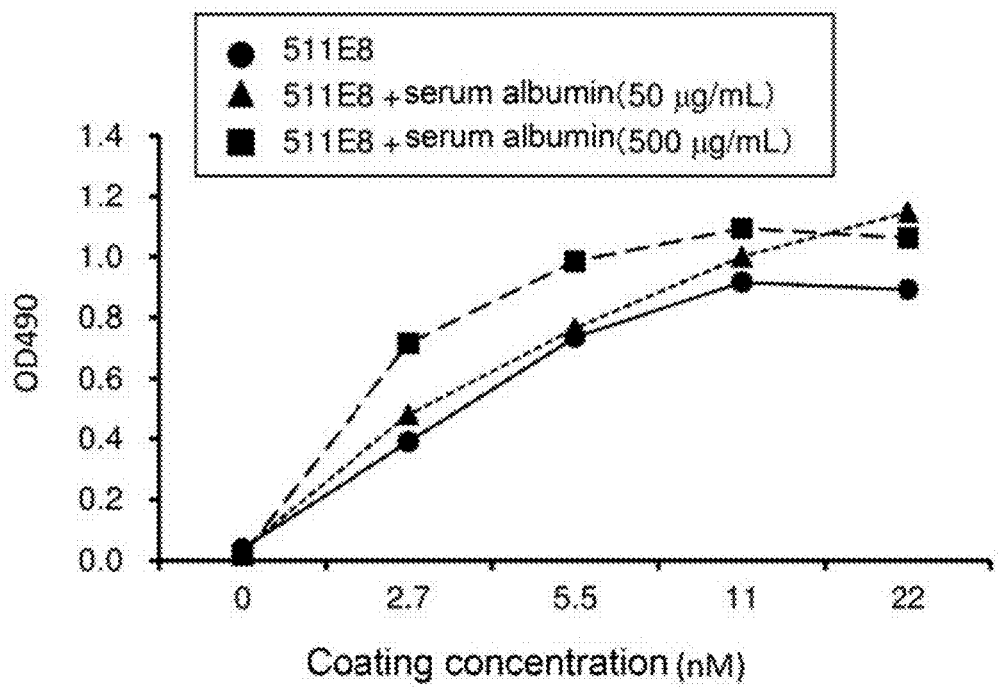
FIG. 1 shows the results of the evaluation of human serum albumin for the effect of enhancing integrin binding activity of laminin 511E8.

In the course of the development of a technology for keeping a laminin fragment stably active in a dry state for a long period of time after coating the surface of a cell culture vessel with the laminin fragment, the present inventors found that, when a cell culture vessel is coated simultaneously with the laminin fragment and a large excess of a protein that is neither a laminin nor a laminin fragment (e.g., gelatin, bovine serum albumin, human serum albumin, etc.; hereinafter referred to as "another protein"), drying-caused reduction in the activity of the laminin fragment can be prevented and thereby the activity of the laminin fragment can be maintained at a level comparable to that without post-coating drying (PCT/JP2014/062449). Furthermore, the present inventors found that simultaneous coating with the laminin fragment and a large excess of another protein not only prevents drying-caused inactivation of the laminin fragment as described above, but also enhances integrin binding activity of the laminin fragment and the growth of human iPS cells on the laminin fragment at a low coating concentration of the laminin fragment.

These findings are specifically as follows. When laminin 511E8 or laminin 521E8 is used alone for coating at concentrations lower than 0.5 μg/cm$^2$ (coating concentration recommended in Non Patent Literature 2), the integrin binding activity and the activity for promoting colony formation of human iPS cells decrease in a coating concentration dependent manner. In contrast, when the same laminin fragment is used in combination with a large excess of another protein for coating at a concentration of half or less of 0.5 μg/cm$^2$, the integrin binding activity and the activity for promoting the growth and colony formation of human iPS cells are comparable to those at a coating concentration of 0.5 μg/cm².

Based on the common knowledge, a large excess of gelatin, serum albumin or the like concomitantly used in coating with the laminin fragment is supposed to competitively block the adsorption of the laminin fragment to a culture vessel, thus considerably compromising coating with the laminin fragment. Such a blocking effect is clearly shown in the art disclosed by Patent Literature 2. Specifically, paragraph [0086] and FIG. 1A of Patent Literature 2 show the following experimental results: when a rat stem cell line (BRL) was cultured on 96-well plates coated with a recombinant laminin 511 (manufactured by BioLamina) and human serum albumin (3.13 to 100 μg/mL), the cell-adhesive activity of laminin 511 in the presence of human serum albumin at a concentration more than 12.5 μg/mL was lower than that in the case of coating with laminin 511 alone. These results strongly indicate that adsorption of laminin 511 was blocked by competition with human serum albumin at a concentration higher than 12.5 μg/mL.

In the present invention, however, even when a laminin fragment and a large excess of gelatin or serum albumin are concomitantly used for coating, no reduction in integrin binding activity is observed, indicating little adverse effect on the amount of the adsorbed laminin fragment. Moreover, it is surprising that, when the coating concentration of the laminin fragment is lower than 0.5 μg/cm², its activity for mammalian cells is enhanced by the large excess of gelatin or serum albumin. This is an unexpected finding. Therefore, although the mechanism for this phenomenon is unclear, it is obvious that the present invention is completely different from the invention disclosed in Patent Literature 2, and the present invention is not easily conceivable based on the invention disclosed in Patent Literature 2.

Furthermore, the present inventors found that, when a laminin fragment diluted to a ready-to-use concentration for coating coexists with a large excess of "another protein" in a solution, the activity of the laminin fragment can be stably maintained without loss. In general, it is empirically known that, when a diluted protein solution is stored in a container such as a glass bottle, the effective concentration of the protein in the solution is reduced due to the adsorption of the protein on the surface of the container. The present inventors actually observed that the activity of a laminin fragment in a solution in the absence of a large excess of "another protein" decreased with time during the storage. Based on the novel findings described above, the present inventors completed a coating solution that does not need dilution or other procedures before use, is usable right out of a refrigerator, and can be kept refrigerated in a stable condition for a long period of time.

<Activity-Enhancing Method>

The present invention provides a method for enhancing an activity for mammalian cultured cells of a laminin fragment or a variant thereof each having integrin binding activity. The activity for mammalian cultured cells means activity as a culture matrix for mammalian cells, and encompasses activity for binding to integrin and other cell-surface adhesion receptors, cell-adhesive activity, cell growth-supporting activity, colony formation-promoting activity, etc.

In the activity-enhancing method of the present invention, the culture surface of a cell culture vessel is brought into contact with a coating solution containing a laminin fragment or a variant thereof and a protein that is neither a laminin nor a laminin fragment ("another protein") in order to achieve coating of the culture surface with the laminin fragment or a variant thereof. The cell culture vessel is not particularly limited as long as it is usable for the culture of mammalian cells. Basically, the cell culture vessel is preferably usable for the culture of mammalian stem cells, more preferably usable for the culture of human stem cells, and still more preferably usable for the culture of human pluripotent stem cells. The cell culture vessel is not limited to vessels in the shape of a container, such as dishes, and may be a vessel in a planar or bead shape. Specific examples of the cell culture vessel include glass or plastic dishes, culture flasks, multiwell plates, culture slides and microcarriers, and polymer membranes such as a polyvinylidene fluoride membrane.

Laminin is a heterotrimeric molecule consisting of three subunits termed α, β and γ chains. Five kinds of α chains (α1 to α5), three kinds of β chains (β1 to β3) and three kinds of γ chains (γ1 to γ3) are known, and various combinations of these chains result in at least 12 kinds of laminin isoforms. A laminin fragment means a molecule in which one or more of the α, β and γ chains of the heterotrimeric structure are shorter than the corresponding full-length chains. The laminin fragment used in the present invention is preferably a heterotrimeric laminin fragment. The heterotrimer formation of the laminin fragment can be confirmed from, for example, the number of bands detected by SDS-PAGE or the elution profile of gel filtration chromatography.

The laminin fragment used in the present invention preferably has integrin binding activity. More preferred is a heterotrimeric laminin fragment having integrin binding activity. A preferable example of such a laminin fragment is a laminin E8 fragment (hereinafter referred to as "laminin E8"). The laminin E8 was identified as a fragment having stronger cell-adhesive activity among the fragments obtained by elastase digestion of mouse laminin α1β1γ1 (hereinafter referred to as "mouse laminin 111") (Edgar D., Timpl R., Thoenen H. The heparin-binding domain of laminin is responsible for its effects on neurite outgrowth and neuronal survival. EMBO J., 3: 1463-1468, 1984; and Goodman SL., Deutzmann R., von der Mark K. Two distinct cell-binding domains in laminin can independently promote nonneuronal cell adhesion and spreading. J. Cell Biol., 105: 589-598, 1987). Elastase digestion of laminins other than mouse laminin 111 could presumably produce fragments corresponding to the mouse laminin 111E8, but there is no report on isolation or identification of such E8 fragments. Therefore, the laminin E8 used in the present invention does not have to be an elastase-digested product of laminins, and may be any laminin fragment having a cell-adhesive activity, structure and molecular weight equivalent to those of the mouse laminin 111E8.

As for the integrin binding activity of the laminin fragment or a variant thereof, there is no particular limitation on the kind of the integrin. Preferred are integrin α6β1, integrin α6β4, integrin α3β1 and integrin α7β1. A preferable example of the laminin fragment having the activity for binding to such a kind of integrin is a laminin fragment derived from at least one kind selected from laminin 511, laminin 521, laminin 411, laminin 421, laminin 311, laminin 321, laminin 332, laminin 211, laminin 221, laminin 111 and laminin 121. More preferred is a laminin fragment derived from at least one kind selected from laminin 511, laminin 521, laminin 411 and laminin 211. Still more preferred is a laminin fragment derived from at least one kind selected from laminin 511 and laminin 521. The integrin binding activity of the laminin fragment can be confirmed by, for example, a solid-phase binding assay using the integrin of interest.

Human stem cells, in particular human pluripotent stem cells are known to more highly express α6β1 integrin than other integrins (Miyazaki T, Futaki S., Hasegawa K., Kawasaki M., Sanzen N., Hayashi M., Kawase E., Sekiguchi K., Nakatsuji N., Suemori H. Recombinant human laminin isoforms can support the undifferentiated growth of human embryonic stem cells. Biochem. Biophys. Res. Commun., 375: 27-32, 2008). Integrin α6β1 binds to various laminin isoforms, but particularly strongly binds to α5 chain-containing laminins, for example, laminin 511 and laminin 521 (Taniguchi Y., Ido H., Sanzen N., Hayashi M., Sato-Nishiuchi R., Futaki S., Sekiguchi K. The C-terminal region of laminin β chains modulates the integrin binding affinities of laminins. J. Biol. Chem., 284: 7820-7831, 2009). Therefore, laminin fragments derived from at least one kind selected from laminin 511 and laminin 521 are particularly preferably used as a culture matrix for human stem cells.

The origin of the laminin fragment is not particularly limited and laminin fragments of various organisms can be used. Preferred are laminin fragments of mammals, including but not limited to humans, mice, rats, cattle and pigs. Particularly preferred is a human laminin fragment. In the human stem cell culture for preparation of materials for human regenerative medicine, a xeno-free (no xenogeneic components are contained in the culture system) environment is required, and for this reason, a human laminin fragment is preferably used.

The laminin fragment may be a native laminin fragment or a modified laminin fragment that has modification of one or more amino acid residues but retains biological activities of the native laminin fragment. The method for producing the laminin fragment is not particularly limited. For example, the laminin fragment can be obtained by digestion of a full-length laminin with a protease such as elastase, followed by isolation and purification of the fragment of interest. Alternatively, the laminin fragment can be produced as a recombinant protein. In terms of production quantity, quality uniformity, production cost, etc., it is preferred that the laminin fragment is produced as a recombinant protein. The full-length laminin can be produced by purification from highly laminin-expressing cells or produced as a recombinant protein (Hiroyuki Ido, Kenji Harada, Sugiko Futaki, Yoshitaka Hayashi, Ryoko Nishiuchi, Yuko Natsuka, Shaoliang Li, Yoshinao Wada, Ariana C. Combs, James M. Ervasti, and Kiyotoshi Sekiguchi, "Molecular dissection of the α-dystroglycan- and integrin-binding sites within the globular domain of human laminin-10" The Journal of Biological Chemistry, 279, 10946-10954, 2004), for example.

The recombinant laminin fragment can be produced by known recombinant techniques. For example, the recombinant laminin and the recombinant laminin fragment can be produced by preparing DNAs encoding full-length or partial-length laminin α, β and γ chains, inserting the DNAs into separate expression vectors, cointroducing the three resulting expression vectors into appropriate host cells, and purifying the expressed trimeric protein by a known method. Examples of the method for producing the recombinant laminin E8 include, but are not limited to, the method of Ido et al. (Hiroyuki Ido, Aya Nakamura, Reiko Kobayashi, Shunsuke Ito, Shaoliang Li, Sugiko Futaki, and Kiyotoshi Sekiguchi, "The requirement of the glutamic acid residue at the third position from the carboxyl termini of the laminin γ chains in integrin binding by laminins" The Journal of Biological Chemistry, 282, 11144-11154, 2007).

Information regarding the nucleotide and amino acid sequences of the genes encoding α, β and γ chains which constitute laminins of major mammals can be obtained from known databases (e.g., GenBank). The accession numbers of the constituent chains of laminins of major mammals including humans are shown in Table 1. Information regarding the nucleotide and amino acid sequences of the constituent chains of laminins of other organisms can also be obtained from known databases (e.g., GenBank).

TABLE 1

| | Amino acid sequence | Nucleotide sequence |
| --- | --- | --- |
| Human laminin α1 chain | NP_005550 | NM_005559 |
| Human laminin α2 chain | NP_000417 | NM_000426 |
| Human laminin α3 chain | NP_000218 | NM_000227 |
| Human laminin α4 chain | NP_002281 | NM_002290 |
| Human laminin α5 chain | NP_005551 | NM_005560 |
| Human laminin β1 chain | NP_002282 | NM_002291 |
| Human laminin β2 chain | NP_002283 | NM_002292 |
| Human laminin β3 chain | NP_000219 | NM_000228 |
| Human laminin γ1 chain | NP_002284 | NM_002293 |
| Human laminin γ2 chain | NP_005553 | NM_005562 |
| Human laminin γ3 chain | NP_006050 | NM_006059 |
| Mouse laminin α5 chain | NP_001074640 | NM_001081171 |
| Mouse laminin β1 chain | NP_032508 | NM_008482 |
| Mouse laminin γ1 chain | NP_034813 | NM_010683 |
| Rat laminin α5 chain | NP_001178538 | NM_001191609 |
| Rat laminin β1 chain | NP_001100191 | NM_001106721 |
| Rat laminin γ1 chain | NP_446418 | NM_053966 |

Laminin E8 is a trimeric fragment composed of a C-terminal fragment of the α chain lacking globular domains 4 and 5 (hereinafter referred to as "α chain E8"), a C-terminal fragment of the β chain (hereinafter referred to as "β chain E8"), and a C-terminal fragment of the γ chain (hereinafter referred to as "γ chain E8"), and the molecular weight of the trimer is about 150 to 170 kDa. The α chain E8 generally consists of about 770 amino acids, of which about 230 amino acids from the N-terminus are involved in the trimer formation. The β chain E8 generally consists of about 220 to 230 amino acids. The γ chain E8 generally consists of about 240 to 250 amino acids. The glutamic acid residue at the third position from the C-terminus of the γ chain E8 is essential for the cell-adhesive activity of laminin E8 (Hiroyuki Ido, Aya Nakamura, Reiko Kobayashi, Shunsuke Ito, Shaoliang Li, Sugiko Futaki, and Kiyotoshi Sekiguchi, "The requirement of the glutamic acid residue at the third position from the carboxyl termini of the laminin 7 chains in integrin binding by laminins" The Journal of Biological Chemistry, 282, 11144-11154, 2007).

The laminin fragment variant used in the present invention is, for example, a chimeric molecule in which a laminin fragment having integrin binding activity is conjugated with a cell adhesion molecule or a growth factor binding molecule (see WO 2012/137970). Preferable examples of the cell adhesion molecule include cell adhesion molecules capable of binding to integrins (e.g., fibronectin, collagen, vitronectin, nephronectin, osteopontin, MAEG, tenascin, SVEP1, TGF-β1 latency associated peptide, TGF-β3 latency associated peptide, EMILIN-1 and EMILIN-2); cell adhesion molecules capable of binding to membrane-bound proteoglycans (e.g., fibronectin, vitronectin, nephronectin and laminin); cell adhesion molecules capable of binding to discoidin domain receptors; cell adhesion molecules capable of binding to dystroglycans (e.g., laminin); and cell adhesion molecules capable of binding to cell-surface sugar chains (e.g., concanavalin A, *Dolichos biflorus* agglutinin, *Arachis hypogaea* agglutinin, *Ricinus communis* agglutinin and wheat germ agglutinin).

Preferable examples of the growth factor binding molecule include heparan sulphate proteoglycans such as perlecan, agrin, type XVIII collagen, syndecans 1 to 4 and glypicans 1 to 6; and latent TGF-β binding proteins 1 to 4.

The chimeric molecule in which a laminin fragment having integrin binding activity is conjugated with a cell adhesion molecule or a growth factor binding molecule can be produced as a recombinant protein by known recombinant techniques. Information regarding the nucleotide and amino acid sequences of the genes encoding known cell adhesion molecules and known growth factor binding molecules can be obtained from known databases (e.g., GenBank).

The activity-enhancing method of the present invention is characterized in that the culture surface of a cell culture vessel is brought into contact with a coating solution containing a laminin fragment or a variant thereof (hereinafter referred to as "a laminin fragment or the like") and a protein that is neither a laminin nor a laminin fragment ("another protein") in order to achieve coating of the culture surface with the laminin fragment or the like. The "another protein" is not limited, and any protein may be used in the present invention. The "another protein" is preferably a water soluble protein. The molecular weight of the "another protein" is not particularly limited, but is preferably 10000 or higher, more preferably 15000 or higher, still more preferably 20000 or higher, still more preferably 30000 or higher, still more preferably 40000 or higher, and still more preferably 60000 or higher.

Specific examples of the "another protein" include gelatin, serum albumin, transferrin, myelin basic protein, β-lactoglobulin, glutathione S-transferase, sericin and collagen. Preferred are gelatin, serum albumin, transferrin, myelin basic protein, β-lactoglobulin, glutathione S-transferase and collagen. More preferred are gelatin, human serum albumin, bovine serum albumin and transferrin. Still more preferred are gelatin and human serum albumin. The "another protein" may be of only one kind or a combination of two or more kinds. The "another protein" is preferably a human protein. This is because human stem cell culture for preparation of materials for human regenerative medicine requires a xeno-free (no xenogeneic components are contained in the culture system) environment.

In the case where gelatin is used as the "another protein", known gelatins for cell culture use are preferably used. More preferred are gelatins that have been confirmed safe for medical use. Examples of the gelatins that have been confirmed safe for medical use include high-grade gelatin and MEDIGELATIN, both of which are available from Nippi, Inc.

The laminin fragment or the like is present in the coating solution in an amount adjusted for the desired coating concentration on the culture surface of a cell culture vessel. The coating concentration is preferably lower than 0.5 µg/cm$^2$, more preferably 0.4 µg/cm$^2$ or lower, still more preferably 0.3 µg/cm$^2$ or lower, still more preferably 0.25 µg/cm$^2$ or lower, still more preferably 0.2 µg/cm$^2$ or lower, still more preferably 0.15 µg/cm$^2$ or lower, still more preferably 0.125 µg/cm$^2$ or lower, and still more preferably 0.1 µg/cm$^2$ or lower. Although the lower limit is not particularly specified, the coating concentration is preferably 0.01 µg/cm$^2$ or higher, and more preferably 0.05 µg/cm$^2$ or higher.

As used herein, the coating concentration is the weight of the laminin fragment or the like per unit area (1 cm$^2$) of the culture surface of a cell culture vessel coated with the laminin fragment or the like. Therefore, the coating concentration is determined by the culture surface area (usable surface area) of the cell culture vessel and the volume of the coating solution. The usable surface areas of typical cell culture vessels and the volumes required for coating these cell culture vessels (standard volume enough for a solution to cover the entire culture surface) are shown in Table 2. The values of the usable surface area are adapted from "the general catalog of cell culture & cell biology products, revised on April, 2014 (Corning Incorporated)". The values of the volume required for coating are based on the volumes used in routine practice by the present inventors.

TABLE 2

| Cell culture vessel | Usable surface area (cm$^2$) | Coating solution volume (mL) |
|---|---|---|
| 35 mm dish | 9.6 | 0.9-1.5 |
| 60 mm dish | 21.3 | 2.2-3.3 |
| 96-well plate | 0.32 | 0.05-0.075 |
| 48-well plate | 0.75 | 0.1-0.15 |
| 24-well plate | 1.88 | 0.3-0.45 |
| 12-well plate | 3.38 | 0.5-0.8 |
| 6-well plate | 9.60 | 0.9-1.5 |

Based on the values shown in Table 2, the concentration of the laminin fragment or the like in the coating solution is preferably 5.0 µg/mL or lower, more preferably 4.5 µg/mL or lower, still more preferably 4.0 µg/mL or lower, still more preferably 3.5 µg/mL or lower, still more preferably 3.0 µg/mL or lower, still more preferably 2.5 µg/mL or lower, still more preferably 2.0 µg/mL or lower, and still more preferably 1.5 µg/mL or lower. Although the lower limit is not particularly specified, the concentration is preferably 0.25 µg/mL or higher, more preferably 0.5 µg/mL or higher, and still more preferably 1.0 µg/mL or higher.

The "another protein" is preferably present in the coating solution in a large excess relative to the laminin fragment or the like. In other words, the "another protein" concomitantly used with the laminin fragment or the like is preferably present in an amount that is supposedly enough to exhibit the blocking effect and thus considerably compromise coating with the laminin fragment or the like. Thus, a technical feature of the activity-enhancing method of the present invention is that, even when a large excess of the "another protein" is used concomitantly with the laminin fragment or the like for coating, the anticipated blocking does not occur, and actually, the activity of the laminin fragment or the like at a low coating concentration is enhanced.

The concentration of the "another protein" in the coating solution is preferably 10-fold or more, more preferably 20-fold or more, still more preferably 30-fold or more, still more preferably 40-fold or more, still more preferably 50-fold or more, still more preferably 60-fold or more, still more preferably 70-fold or more, still more preferably 80-fold or more, still more preferably 90-fold or more, and still more preferably 100-fold or more that of the laminin fragment or the like in the coating solution. The upper limit is not particularly specified and any appropriate concentration can be selected as long as the activity-enhancing effect can be produced. Typically, the concentration of the "another protein" in the coating solution is 2000-fold or less that of the laminin fragment or the like in the coating solution.

The concentration of the "another protein" in the coating solution is preferably 50 µg/mL or higher, more preferably 100 µg/mL or higher, still more preferably 150 µg/mL or higher, still more preferably 200 µg/mL or higher, still more preferably 250 µg/mL or higher, still more preferably 300

μg/mL or higher, still more preferably 350 μg/mL or higher, still more preferably 400 μg/mL or higher, still more preferably 450 μg/mL or higher, and still more preferably 500 μg/mL or higher. The upper limit is not particularly specified and any appropriate concentration can be selected as long as the activity-enhancing effect can be produced. Typically, the concentration of the "another protein" in the coating solution is 5 mg/mL or lower, and preferably 1 mg/mL or lower.

For preparation of the coating solution, the laminin fragment or the like of interest and the "another protein" of interest are dissolved at desired concentrations in an appropriate solvent. The solvent usable in the coating solution is not particularly limited unless the solvent reduces the activity of proteins, but preferred is an aqueous solvent. Neutral buffers, which are commonly used as solvents for proteins, are preferably used. Specific examples of the neutral buffers include a physiological saline adjusted to a near-neutral pH with phosphoric acid, citric acid, boric acid, acetic acid, tris(hydroxymethyl)aminomethane, HEPES (4-(2-hydroxyethyl)-1-piperazineethanesulfonic acid) or the like. The coating solution is preferably subjected to sterilization such as filter sterilization before use.

The coating solution preferably contains all the proteins of interest (the laminin fragment or the like and the "another protein"), but a coating solution containing the laminin fragment or the like and a coating solution containing the "another protein" may be separately prepared and then mixed on the culture surface of a cell culture vessel.

The coating operation is not particularly limited, and any appropriate procedure can be used for coating. For example, the entire culture surface of a cell culture vessel is brought into contact with the coating solution(s), and incubation is performed with or without gentle agitation for a certain period of time, so that the culture surface of the cell culture vessel can be coated with the proteins contained in the coating solution(s). In the case of a cell culture vessel in the shape of a container, the coating solution(s) is/are placed in the container. In the case of a sheet- or film-shaped cell culture vessel, the coating solution(s) is/are applied on top of the area to be coated. The coating conditions are not particularly limited, but typically, incubation is performed at 4° C. for about 2 to 18 hours or at room temperature up to 37° C. about 0.5 to 6 hours. After a given time, the coating solution placed or applied is removed. The coated surface is preferably washed after the removal of the coating solution. The wash solution is not particularly limited, but buffered physiological saline solutions such as PBS are preferably used. The coating operation is preferably performed in a sterile place such as a clean room and a clean bench.

The coated cell culture vessel can be used for cell culture as it is, but drying the coated surface may follow the coating operation. Once the coated surface is dried, the cell culture vessel can be stored. The drying method is not particularly limited, and well-known drying methods such as air drying and reduced pressure drying can be used. The drying temperature is not particularly limited unless it causes denaturation or inactivation of the proteins adsorbed on the surface, but room temperature is suitable. The drying temperature is usually about 2 to 40° C., preferably about 4 to 37° C., more preferably about 10 to 30° C., and still more preferably about 15 to 25° C. The drying time is not particularly limited, and drying can be finished once the coated surface is visually confirmed dry without residual liquid. It is preferable to determine in advance an optimal drying time depending on the conditions such as the shape of the cell culture vessel, the composition of the coating solution, the drying method and the drying temperature. The drying operation is preferably performed in a sterile place such as a clean room and a clean bench.

After drying the proteins adsorbed on the surface, the step of sterilizing the dried proteins may be additionally performed. Preferable examples of the sterilizing method include radiation sterilization, such as electron beam sterilization and X-ray sterilization, and ultraviolet radiation sterilization. It is better not to use sterilization methods having the risk of denaturing proteins, such as chemical sterilization including ethylene oxide gas sterilization, and autoclave sterilization using moist heat. In the case where the sterilization step is additionally performed, the production of the cell culture vessel of the present invention is not necessarily performed under strictly sterile conditions and therefore can be achieved at low cost. The cell culture vessel with the coated surface in a dry state can be stably stored in a hermetically sealed package for a long period of time. The storage temperature is preferably room temperature or lower, and more preferably a further lower temperature (for example, about 4° C.)

It is experimentally shown that, when the laminin fragment or the like is used alone for coating at a concentration lower than the recommended concentration (0.5 μg/cm$^2$: Non Patent Literature 2, for example), the activities of the laminin fragment or the like, such as integrin binding activity, cell-adhesive activity, cell growth-supporting activity and colony formation-promoting activity, are reduced. However, according to the activity-enhancing method of the present invention, when the coating concentration of the laminin fragment or the like is lower than the recommended coating concentration, such activities are enhanced, and thus, cell culture can be achieved as in the case where the laminin fragment or the like is used alone for coating at the recommended concentration. The activity-enhancing method of the present invention enables the reduction of the amount of the laminin fragment or the like used for coating, leading to greatly curbing the cost for coating.

<Culture Method>

The culture method of the present invention is a method for culturing mammalian cells using the above-described activity-enhancing method of the present invention, that is, a method for culturing mammalian cells using a cell culture vessel coated with a laminin fragment or the like at a concentration lower than the recommended concentration in combination with a large excess of "another protein". The cell culture vessel used in the culture method of the present invention is the same as described above in the activity-enhancing method of the present invention.

The culture method of the present invention is applicable to the culture of any mammalian cells, but is preferably applied to the culture of stem cells. The stem cells refer to cells having a self-renewal capacity and pluripotency, and include somatic stem cells and pluripotent stem cells. Examples of the somatic stem cells include neural stem cells, mesenchymal stem cells and hematopoietic stem cells. Examples of the pluripotent stem cells include ES cells (embryonic stem cells), iPS cells (induced pluripotent stem cells), mGS cells (multipotent germ stem cells) and hybridomas of ES cells and somatic cells. Pluripotent stem cells are more preferred, and ES cells and iPS cells are still more preferred. In addition, the culture method of the present invention is also suitable for the culture of cells differentiated from the above-mentioned stem cells. The cells differentiated from the stem cells include various cells derived via directed differentiation of the stem cells. That is, the culture method of the present invention is suitable for the culture of cells of different stages in the differentiation process of stem cells towards terminally differentiated cells. The mammal as the origin of the cells is not particularly limited, and the examples include humans, mice, rats, cattle and pigs. Particularly preferred are humans. That is, the culture method of the present invention is preferably used for the culture of human stem cells and cells differentiated therefrom. In the case where the culture method of the present invention is used for the culture of human stem cells and cells differentiated therefrom, a human laminin fragment or a variant thereof is preferably used.

The culture medium used for mammalian cell culture in the culture method of the present invention is not particularly limited, and a known recommended culture medium can be used depending on the cell type. The detailed culture procedure is also not particularly limited, and a known recommended culture procedure is preferably employed depending on the cell type.

<Coating Solution>

The present invention provides a coating solution containing a laminin fragment or the like having integrin binding activity and "another protein" in a large excess relative to the laminin fragment or the like. The coating solution of the present invention is suitable as a coating solution for use in the above-described activity-enhancing method and culture method of the present invention.

The laminin fragment or the like contained in the coating solution of the present invention is preferably the laminin fragment or a variant thereof described above in the activity-enhancing method of the present invention. The "another protein" contained in the coating solution of the present invention is preferably the protein that is neither a laminin nor a laminin fragment ("another protein") described above in the activity-enhancing method of the present invention.

The coating solution of the present invention preferably contains a laminin fragment or the like at a concentration of 5.0 µg/mL or lower and "another protein" at a concentration of 50 µg/mL or higher. The concentration of the laminin fragment or the like in the coating solution is more preferably 4.5 µg/mL or lower, still more preferably 4.0 µg/mL or lower, still more preferably 3.5 µg/mL or lower, still more preferably 3.0 µg/mL or lower, still more preferably 2.5 µg/mL or lower, still more preferably 2.0 µg/mL or lower, and still more preferably 1.5 µg/mL or lower. Although the lower limit is not particularly specified, the concentration is preferably 0.25 µg/mL or higher, more preferably 0.5 µg/mL or higher, and still more preferably 1.0 µg/mL or higher.

The concentration of the "another protein" in the coating solution is preferably 10-fold or more, more preferably 20-fold or more, still more preferably 30-fold or more, still more preferably 40-fold or more, still more preferably 50-fold or more, still more preferably 60-fold or more, still more preferably 70-fold or more, still more preferably 80-fold or more, still more preferably 90-fold or more, and still more preferably 100-fold or more that of the laminin fragment or the like in the coating solution. The upper limit is not particularly specified, but typically, the concentration of the "another protein" in the coating solution is 2000-fold or less that of the laminin fragment or the like in the coating solution.

The concentration of the "another protein" in the coating solution is preferably 50 µg/mL or higher, more preferably 100 µg/mL or higher, still more preferably 150 µg/mL or higher, still more preferably 200 µg/mL or higher, still more preferably 250 µg/mL or higher, still more preferably 300 µg/mL or higher, still more preferably 350 µg/mL or higher, still more preferably 400 µg/mL or higher, still more preferably 450 µg/mL or higher, and still more preferably 500 µg/mL or higher. The upper limit is not particularly specified, but typically, the concentration of the "another protein" in the coating solution is 5 mg/mL or lower, and preferably 1 mg/mL or lower.

It is preferred that the coating solution of the present invention can be used for coating as it is without dilution before use. Therefore, it is preferred that the concentration of the laminin fragment or the like in the coating solution is adjusted so that the coating concentration of the laminin fragment or the like on the culture surface of a cell culture vessel is lower than 0.5 µg/cm$^2$. The coating concentration of the laminin fragment or the like is more preferably 0.4 µg/cm$^2$ or lower, still more preferably 0.3 µg/cm$^2$ or lower, still more preferably 0.25 µg/cm$^2$ or lower, still more preferably 0.2 µg/cm$^2$ or lower, still more preferably 0.15 µg/cm$^2$ or lower, still more preferably 0.125 µg/cm$^2$ or lower, and still more preferably 0.1 µg/cm$^2$ or lower.

For preparation of the coating solution, the laminin fragment or the like of interest and the "another protein" of interest are dissolved at desired concentrations in an appropriate solvent. The solvent usable in the coating solution is not particularly limited unless the solvent reduces the activity of proteins, but preferred is an aqueous solvent. Neutral buffers, which are commonly used as solvents for proteins, are preferably used. Specific examples of the neutral buffers include a physiological saline adjusted to a near-neutral pH with phosphoric acid, citric acid, boric acid, acetic acid, tris(hydroxymethyl)aminomethane, HEPES (4-(2-hydroxyethyl)-1-piperazineethanesulfonic acid) or the like. The coating solution is preferably subjected to sterilization such as filter sterilization before use.

The coating solution of the present invention may contain another component in addition to the laminin fragment or the like, the "another protein" and the solvent component unless the intended purpose is hindered, but preferably, the coating solution contains no component except the laminin fragment or the like, the "another protein" and the solvent component. In a preferable embodiment, the coating solution of the present invention is stored in an appropriate container with an appropriate capacity. The container is not particularly limited, and known containers usable for the storage of protein solutions are preferably used. The container is preferably a hermetically sealed container and is preferably a light-resistant container. The coating solution of the present invention is preferably provided together with an attached document describing the volumes of the coating solution and the coating concentrations suitable for coating various types of cell culture vessels. Thus, an embodiment of the present invention is a kit for coating with a laminin fragment or the like, the kit comprising the coating solution of the present invention stored in an appropriate container and the above-described attached document.

The coating solution of the present invention is preferably kept refrigerated at a temperature of 10° C. or lower in a hermetically sealed container. The temperature is more preferably 3 to 5° C. The coating solution of the present invention is preferably stored away from light for protection of proteins from UV-induced denaturation. The present inventors have confirmed that the coating solution of the present invention at a ready-to-use concentration can be kept refrigerated in a stable condition for at least 12 months, and have been examining the effect of longer-term storage.

The coating solution of the present invention does not need to be prepared (thawing, dissolution, dilution, etc. of frozen stock solutions) immediately before use and can be kept refrigerated in a stable condition for a long period of time. Therefore, a coating operation can be quickly accomplished simply by taking out the coating solution of the present invention from a refrigerator before use and placing/applying a given volume of the coating solution into/on a culture vessel. Such a short-time and simple coating operation is a great advantage. In addition, cell culture vessels can always be coated at the same concentration regardless of when and by whom a coating operation is carried out because the coating solution kept refrigerated can be repeatedly used.

EXAMPLES

Hereinafter, the present invention will be illustrated in detail by examples, but the present invention is not limited thereto.

<Preparation of Human Recombinant Laminin 511E8>

Human recombinant laminin 511E8 (hereinafter referred to as "511E8") was prepared according to the method of Ido et al. (Hiroyuki Ido, Aya Nakamura, Reiko Kobayashi, Shunsuke Ito, Shaoliang Li, Sugiko Futaki, and Kiyotoshi Sekiguchi, "The requirement of the glutamic acid residue at the third position from the carboxyl termini of the laminin γ chains in integrin binding by laminins" The Journal of Biological Chemistry, 282, 11144-11154, 2007) as follows.

First, a cloning plasmid pBluescript KS(+) (Stratagene) was used as a template for PCR with three sets of primers to prepare three kinds of pBluescript KS(+) containing a DNA encoding a 6×His tag, a DNA encoding an HA (hemagglutinin) tag or a DNA encoding a FLAG tag inserted at the 5' end of the EcoRV site in the multicloning site. The three sets of primers used for the PCR are as follows.

```
(i) Primers for 6×His tag insertion
(forward, SEQ ID NO: 1)
5'-ATGATGATGAAGCTTATCGATACCGT-3'

(reverse, SEQ ID NO: 2)
5'-CATCATCATGATATCGAATTCCTGCA-3'

(ii) Primers for HA tag insertion
(forward, SEQ ID NO: 3)
5'-ATCATATGGATAAAGCTTATCGATACCGT-3'

(reverse, SEQ ID NO: 4)
5'-GTGCCAGATTATGCAGATATCGAATTCCT-3'

(iii) Primers for FLAG tag insertion
(forward, SEQ ID NO: 5)
5'-ATCCTTTGTAATCAAGCTTATCGATACCGT-3'

(reverse, SEQ ID NO: 4)
5'-GTGCCAGATTATGCAGATATCGAATTCCT-3'
```

Next, plasmids containing the full-length nucleotide sequences of the α5, β1 and γ1 chains (Ido et al., J. Biol. Chem., 279, 10946-10954, 2004) were used as templates for PCR with three sets of primers to amplify the region corresponding to α5 chain E8 (Ala$^{2534}$-Ala$^{3327}$), the region corresponding to β1 chain E8 (Leu$^{1561}$-Leu$^{1786}$) and the region corresponding to γ1 chain E8 (Asn$^{1362}$-Pro$^{1608}$). The primers used for the PCR are as follows.

```
(iv) Primers for amplifictaion of α5 chain
E8 fragment
(forward, SEQ ID NO: 6)
5'-GCTGCCGAGGATGCTGCTGGCCAGG-3'

(reverse, SEQ ID NO: 7)
5'-CTAGGCAGGATGCCGGGCGGGCTGA-3'

(v) Primers for amplifictaion of β1 chain
E8 fragment
(forward, SEQ ID NO: 8)
5'-CTTCAGCATAGTGCTGCTGACATTG-3'

(reverse, SEQ ID NO: 9)
5'-TTACAAGCATGTGCTATACACAGCAAC-3'

(vi) Primers for amplifictaion of γ1 chain
E8 fragment
(forward, SEQ ID NO: 10)
5'-AATGACATTCTCAACAACCTGAAAG-3'

(reverse, SEQ ID NO: 11)
5'-CTAGGGCTTTTCAATGGACGGGGTG-3'
```

The amplified cDNAs were separately inserted into the EcoRV site in the multicloning site of the above-prepared three kinds of pBluescript KS(+) containing a tag-encoding sequence. From each resulting plasmid, the region containing the inserted DNA fragment and the 5'-terminal tag-encoding sequence was amplified. The amplified product was digested with restriction enzymes EcoRI and HindIII. The digested fragment was inserted into the corresponding restriction site of pSecTag2B, a mammalian cell expression vector (Invitrogen), to give an expression vector for the human α5 chain E8 fragment (containing the 6×His tag in the N-terminal region), an expression vector for the human β1 chain E8 fragment (containing the HA tag in the N-terminal region), and an expression vector for the human γ1 chain E8 fragment (containing the FLAG tag in the N-terminal region).

For expression of 511E8, the three expression vectors were introduced into human embryonic kidney 293F cells (purchased from Invitrogen). Into 300 mL of 293F cells ($1.0×10^6$ cells/mL), 180 μg each of the three expression vectors were co-transfected with transfection reagents 293fectin (trade name, Invitrogen) and Opti-MEM (trade name, Invitrogen). The transfected cells were cultured for 72 hours, and the culture medium was then harvested. The harvested culture medium was centrifuged at 1,000×g for 10 minutes, and the supernatant was further centrifuged at 15,000×g for 30 minutes for removal of remaining cells and insoluble matter. To the supernatant, 5 mL of Ni-NTA agarose (QIAGEN) was added and the protein of interest was allowed to bind thereto by overnight incubation. The Ni-NTA agarose was collected and washed successively with TBS(−) (tris-buffered saline without Ca or Mg) and 10 mM imidazole/TBS(−). Elution was performed with 200 mM imidazole/TBS(−). The eluted fractions were subjected to SDS-PAGE followed by silver staining. To the 511E8-containing fraction, 2 mL of ANTI-FLAG M2 Affinity Gel (Sigma) was added and the mixture was rotated at 4° C. overnight. The affinity gel was transferred into an Econo Column, which was then washed with TBS(−) containing 1 mM PMSF. Subsequently, elution was performed with TBS (−) containing 100 μg/mL FLAG peptide (Sigma). After the eluted fractions were subjected to silver staining, the 511E8-containing fractions were combined and dialyzed against TBS(−).

<Preparation of Human Recombinant Laminin 521E8>

Human recombinant laminin 521E8 (hereinafter referred to as "521E8") was prepared similarly as described above for human recombinant laminin 511E8. The specific procedure is as follows. An expression vector for the human α5 chain E8 fragment (containing the 6×His tag in the N-terminal region), an expression vector for the human β2 chain E8 fragment (containing the HA tag in the N-terminal region), and an expression vector for the human γ1 chain E8 fragment (containing the FLAG tag in the N-terminal region) were prepared and then transfected into human embryonic kidney 293F cells. The transfected cells were cultured for 72 hours and the culture medium was then harvested. Subsequently, affinity chromatographic purification using Ni-NTA agarose and ANTI-FLAG M2 Affinity Gel was performed as was the case with the laminin 511E8. The expression vector for the human β2 chain E8 fragment was prepared according to the method of Taniguchi et al. (Yukimasa Taniguchi, Hiroyuki Ido, Noriko Sanzen, Maria Hayashi, Ryoko Sato-Nishiguti, Sugiko Futaki, and Kiyotoshi Sekiguchi, "The C-terminal region of laminin β chains modulates the integrin binding affinities of laminins" The Journal of Biological. Chemistry, 284, 7820-7831, 2009).

<Preparation of Human Recombinant Laminin 211E8 and Laminin 411E8>

Human recombinant laminin 211E8 (hereinafter referred to as "211E8") and laminin 411E8 (hereinafter referred to as "411E8") were prepared similarly as described above for human recombinant laminin 511E8. The specific procedure is as follows. An expression vector for the human α2 chain E8 fragment or the human α4 chain E8 fragment (each containing the 6×His tag in the N-terminal region), an expression vector for the human β1 chain E8 fragment (containing the HA tag in the N-terminal region), and an expression vector for the human γ1 chain E8 fragment (containing the FLAG tag in the N-terminal region) were prepared and then transfected into human embryonic kidney 293F cells. The transfected cells were cultured for 72 hours and the culture medium was then harvested. Subsequently, affinity chromatographic purification using Ni-NTA agarose and ANTI-FLAG M2 Affinity Gel was performed as was the case with the laminin 511E8. The expression vector for the human α2E8 fragment and the expression vector for the human α4E8 fragment were prepared according to the method of Taniguchi et al. (Yukimasa Taniguchi, Hiroyuki Ido, Noriko Sanzen, Maria Hayashi, Ryoko Sato-Nishiguti, Sugiko Futaki, and Kiyotoshi Sekiguchi, "The C-terminal region of laminin β chains modulates the integrin binding affinities of laminins" The Journal of Biological Chemistry, 284, 7820-7831, 2009).

Example 1: Enhancement of Integrin Binding Activity of 511E8 by "Another Protein"

Experimental Methods
(1) Plate Coating

511E8 was serially diluted to final concentrations of 22 nM, 11 nM, 5.5 nM and 2.7 nM in PBS (Gibco, cat#10010-049, pH 7.4) containing 50 µg/mL or 500 µg/mL human serum albumin (Biological Industries, cat#05-720-1B; hereinafter referred to as HSA). The diluted solutions were added at 50 µL/well to a 96-well plate (Becton Dickinson, #353072, usable surface area: 0.32 cm²/well). The plate was incubated with gentle agitation at 4° C. overnight for coating. The coating concentrations represented as the weight of 511E8 per unit area were 0.5, 0.25, 0.125 and 0.0625 µg/cm². Similarly, 511E8 was serially diluted to final concentrations of 22 nM, 11 nM, 5.5 nM and 2.7 nM in PBS (Gibco, cat#10010-049, pH 7.4) containing 50 µg/mL or 500 µg/mL gelatin (Nippi, Inc., APAT), and a 96-well plate was coated with the diluted solutions. In addition, 511E8 was similarly serially diluted in PBS without HSA or gelatin, and a 96-well plate was coated with the diluted solutions as the control.

(2) Integrin Binding Assay

Integrin binding assay was performed according to the method of Ido et al. (Ido et al., The Journal of Biological Chemistry, 282, 11144-11154, 2007). The specific procedure is as follows. To the 96-well plate coated with 511E8 alone or plus HSA or gelatin (final concentration: 50 µg/mL or 500 µg/mL) as described above, 20 mM Tris buffer (pH 7.4) containing 0.1% bovine serum albumin (BSA; Sigma-Aldrich, cat#A7906), 0.02% Tween-20 (Wako, cat#167-1.1515) and 130 mM NaCl (hereinafter referred to as 0.1% BSA/TBST) was added at 200 µL/well for washing. Next, 20 mM Tris buffer (pH 7.4) containing 1% bovine serum albumin, 0.02% Tween-20 and 130 mM NaCl (hereinafter referred to as 1% BSA/TBST) was added at 200 µL/well to the plate, and the plate was incubated with agitation on a shaker (B. Braun Biotech International, CERTOMAT MT) at room temperature for 1 hour for blocking. After the plate was washed once with 200 µL/well of 0.1% BSA/TBST, an α6β1 integrin solution (10 nM α6β1 integrin, 19.6 mM Tris, 127 mM NaCl, 0.0056% Tween-20, 0.1% BSA, 1 mM $MnCl_2$) was added at 50 µL/well to the plate. The plate was incubated with agitation on the shaker at room temperature for 3 hours in order for the reaction to proceed. After the plate was washed 3 times with 200 µL/well of 1 mM $MnCl_2$/0.1% BSA/TBST, 1 µg/mL of a biotin-labeled anti-Velcro antibody (prepared as described in Takagi, J., Erickson, H. P., and Springer, T. A. (2001) Nat. Struct. Biol. 8, 412-416) diluted in 1 mM $MnCl_2$/0.1% BSA/TBST was added at 50 µL/well to the plate. The plate was incubated on the shaker at room temperature for 30 minutes in order for the reaction to proceed. After the plate was washed 3 times with 200 µL/well of 1 mM $MnCl_2$/0.1% BSA/TBST, 0.6 µg/mL streptavidin-horseradish peroxidase (Pierce, cat#21126) diluted in 1 mM $MnCl_2$/0.1% BSA/TBST was added at 50 µL/well to the plate. The plate was incubated on the shaker at room temperature for 15 minutes in order for the reaction to proceed. After the plate was washed 3 times with 200 µL/well of 1 mM $MnCl_2$/0.1% BSA/TBST, an o-phenylenediamine (OPD) solution (0.04% OPD (Wako, cat#161-11851), 0.04% $H_2O_2$, 25 mM citric acid, 53 mM $Na_2HPO_4$) was added at 50 L/well to the plate. The plate was incubated for 2 minutes and 20 seconds in order for the reaction to proceed. After the reaction was stopped by addition of 2.5 M $H_2SO_4$, the absorbance at 490 nm of the chromogenic substrate was measured with a microplate reader (Molecular Devices EMax).

Experimental Results
(1) Effect of HSA

The results of the measurement of the integrin binding activity on the plate coated with 511E8 plus 50 µg/mL or 500 µg/mL HSA are shown in FIG. 1. The amount of the bound integrin increased along with the increase in the coating concentration of 511E8 regardless of the presence or absence of HSA. The addition of 500 µg/mL HSA clearly increased the integrin binding activity of 511E8. This effect was particularly remarkable in the range of low coating concentrations of 511E8. When the coating concentration of 511E8 was 2.7 nM, the integrin binding activity was increased by 80% or more by the addition of HSA. Also observed was an about 10% increase in the activity with the addition of 50 µg/mL HSA.

(2) Effect of Gelatin

Figure 2:
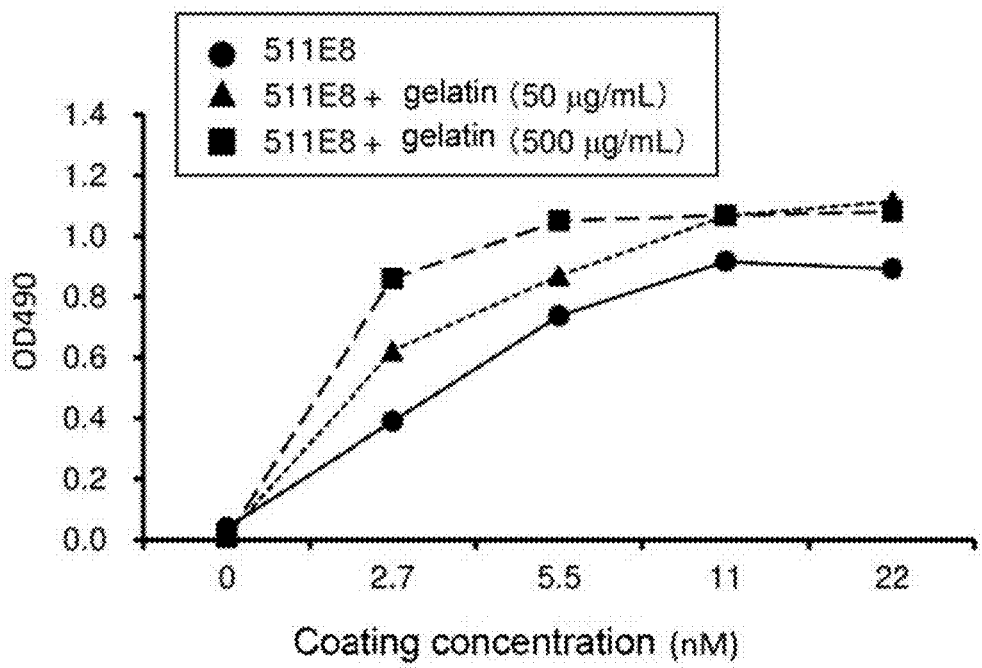
FIG. 2 shows the results of the evaluation of gelatin for the effect of enhancing integrin binding activity of laminin 511E8.

The results of the measurement of the integrin binding activity on the plate coated with 511E8 plus 50 µg/mL or 500

µg/mL gelatin are shown in FIG. 2. The results for the addition of gelatin were similar to those for the addition of HSA. That is, the addition of 500 µg/mL gelatin clearly increased the integrin binding activity of 511E8, and such an activity-enhancing effect was particularly remarkable in the range of low coating concentrations of 511E8. When the coating concentration of 511E8 was 2.7 nM, the integrin binding activity was increased to 2-fold or more by the addition of gelatin. Also observed was a 20 to 60% increase in the activity with the addition of 50 µg/mL gelatin.

The above results show that the integrin binding activity of 511E8 on the plate coated with 511E8 plus HSA or gelatin is significantly higher than that on the plate coated with 511E8 alone. Also shown is that a higher concentration of HSA or gelatin provides a greater increase in the integrin binding activity.

Example 2: Enhancement of Integrin Binding Activity of Laminin 521E8 Fragment by "Another Protein"

Figure 3:
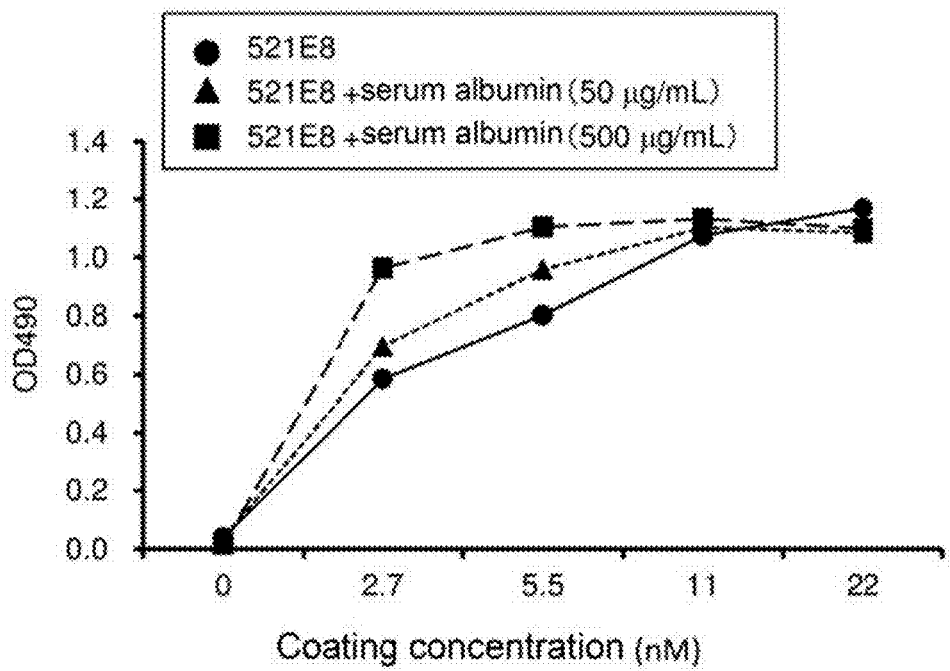
FIG. 3 shows the results of the evaluation of human serum albumin for the effect of enhancing integrin binding activity of laminin 521E8.
Figure 4:
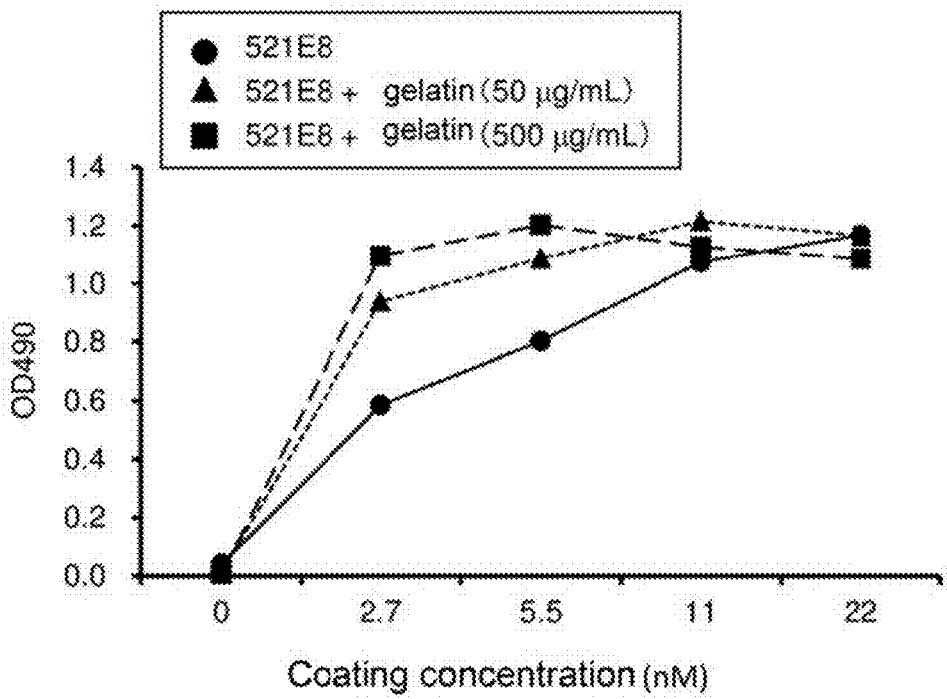
FIG. 4 shows the results of the evaluation of gelatin for the effect of enhancing integrin binding activity of laminin 521E8.

Whether the integrin binding activity of a laminin E8 fragment other than 511E8 would be increased by addition of HSA or gelatin was examined using 521E8.
Experimental Methods
(1) Plate Coating
A plate was coated in the same manner as described in Example 1 except for using 521E8 instead of 511E8.
(2) Integrin Binding Assay
Integrin binding activity was measured in the same manner as described in Example 1.
Experimental Results
(1) Effect of HSA
The results of the measurement of the integrin binding activity on the plate coated with 521E8 plus 50 µg/mL or 500 µg/mL HSA are shown in FIG. 3. As with 511E8, the integrin binding activity of 521E8 was significantly increased by the addition of 500 µg/mL HSA. Such an increase in the integrin binding activity was more remarkable in the range of lower coating concentrations of 521E8. When the coating concentration of 521E8 was 2.7 nM, the integrin binding activity was increased by 60% or more by the addition of 500 µg/mL HSA. Also observed was a 10 to 20% increase in the activity with the addition of 50 µg/mL HSA.
(2) Effect of Gelatin
The results of the measurement of the integrin binding activity on the plate coated with 521E8 plus 50 µg/mL or 500 µg/mL gelatin are shown in FIG. 4. The results for the addition of gelatin were similar to those for the addition of HSA. That is, the addition of 500 µg/mL gelatin clearly increased the integrin binding activity of 521E8, and such an activity-enhancing effect was particularly remarkable in the range of low coating concentrations of 521E8. When the coating concentration of 521E8 was 2.7 nM, the integrin binding activity was increased by 80% or more by the addition of gelatin. Also observed was a 10 to 60% increase in the activity with the addition of 50 µg/mL gelatin.

The above results, taken together, show that the addition of 50 to 500 µg/mL HSA or gelatin to a coating solution significantly increases the integrin binding activities of both 511E8 and 521E8 on the coated plates. Also shown is that a higher concentration of HSA or gelatin provides a more remarkable increase in the integrin binding activities of both 511E8 and 521E8.

Example 3: Human iPS Cell Culture on the Culture Plate Coated with 511E8 Plus "Another Protein"

Figure 5:
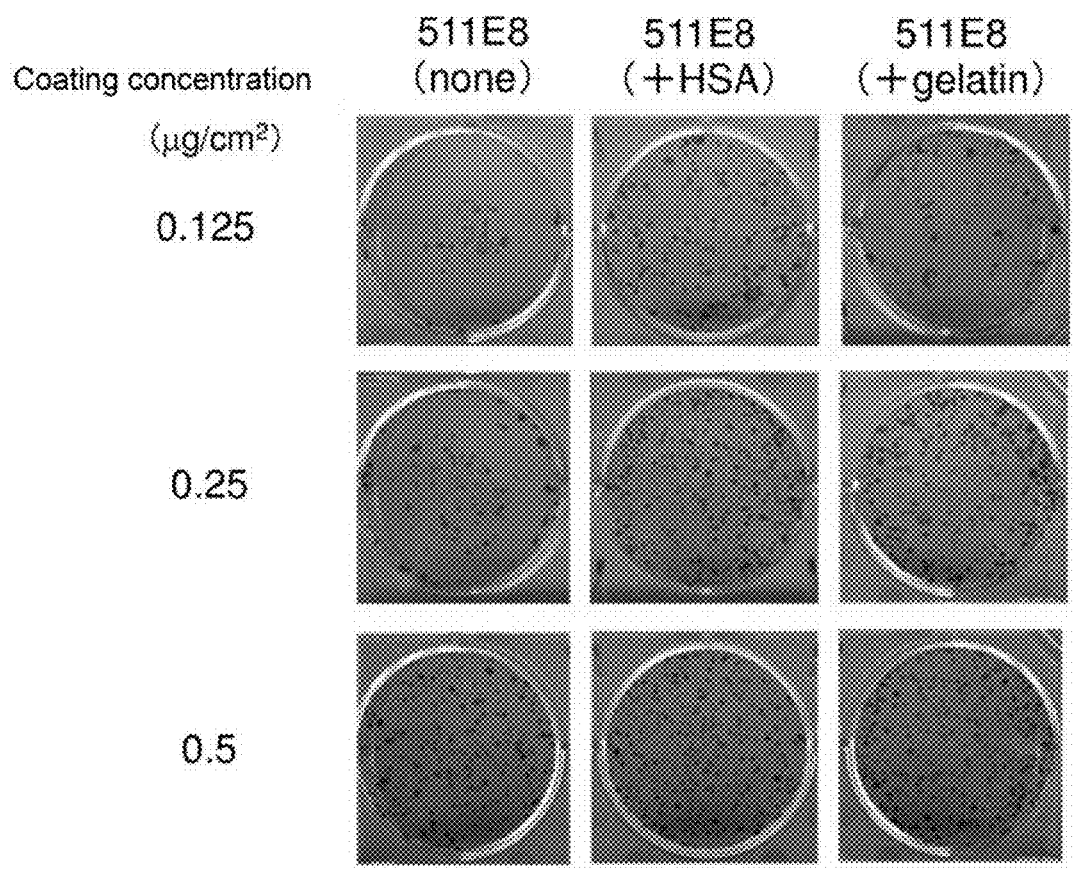
FIG. 5 shows the results of alkaline phosphatase staining of human iPS cells cultured on a culture plate coated with laminin 511E8 plus human serum albumin or gelatin.

Experimental Methods
Whether the activity of 511E8 as a cell culture matrix would be enhanced by HSA or gelatin was examined using a 6-well cell culture plate (Becton Dickinson, cat#353046; usable surface area: 9.6 cm$^2$) coated with 511E8 alone or plus HSA (Biological Industries, cat#05-720-1B) or gelatin (Nippi, Inc., APAT). The cell used was a human induced pluripotent stem (iPS) cell line 201B7, and the culture method used was the method of Nakagawa et al. (Masato Nakagawa, Yukimasa Taniguchi, Sho Senda, Nanako Takizawa, Tomoko Ichisaka, Kanako Asano, Asuka Morizane, Daisuke Doi, Jun Takahashi, Masatoshi Nishizawa, Yoshinori Yoshida, Taro Toyoda, Kenji Osafune, Kiyotoshi Sekiguchi, Shinya Yamanaka, "A novel efficient feeder-free culture system for the derivation of human induced pluripotent stem cells" Scientific Reports 4, 3594, 2014, doi: 10.1038/srep03594). The specific procedure is as follows. 511E8 was serially diluted to 32 nM, 16 nM and 8 nM in PBS (Gibco, cat#10010-049, pH 7.4) containing HSA or gelatin at a final concentration of 500 µg/mL. These 511E8 solutions were added to wells of a plate in such a volume that the coating concentration would be 0.5 µg/cm$^2$, 0.25 µg/cm$^2$ or 0.125 µg/cm$^2$. The plate was incubated with gentle agitation at 4° C. overnight (for about 18 hours) for coating. In addition, 511E8 was serially diluted in PBS without HSA or gelatin, and a plate was similarly coated with these 511E8 solutions in such a volume that the coating concentration would be 0.5 µg/cm$^2$, 0.25 µg/cm$^2$ or 0.125 µg/cm$^2$, as the control. After removal of the coating solution, 201B7 cells prepared by dissociation into single cells with TrypLE Select (Life Technologies, cat#A 12859-01) were seeded at 1.35× 10$^3$ cells/cm$^2$ and cultured for one week. A mixed medium of TeSR2 (STEMCELL Technologies, cat#05860) and NutriStem (Biological Industries, cat#05-100-1) (1:1) was used as culture medium. The culture medium was replaced every other day. After one week of culture, the cells were stained for alkaline phosphatase. The alkaline phosphatase staining was performed using a Leukocyte Alkaline Phosphatase Kit (Sigma-Aldrich, cat#86R-1KT) according to the attached recommended protocol.
Experimental Results
The cells stained for alkaline phosphatase are shown in FIG. 5. When the coating concentration of 511E8 was 0.5 µg/cm$^2$, whether or not HSA or gelatin was added, no significant difference in the number and size of colonies formed from the cells was observed. In contrast, when the coating concentration of 511E8 was 0.25 µg/cm$^2$ or 0.125 µg/cm$^2$, the number of colonies was significantly increased by the addition of HSA or gelatin. In addition, although the coating concentration of 511E8 was half (0.25 µg/cm$^2$) the concentration recommended for human iPS cell culture (0.5 µg/cm$^2$: Non Patent Literature 2), the growth of the iPS cells was almost comparable to that observed at the recommended coating concentration due to the addition of HSA or gelatin. Moreover, when HSA was added at a final concentration of 500 µg/mL, the iPS cells were sufficiently grown even at ¼ (0.125 µg/cm$^2$) of the recommended coating concentration. Also, the human iPS cells cultured on the plate coated with 511E8 plus HSA or gelatin were strongly stained for alkaline phosphatase activity, indicating that the iPS cells were maintained in an undifferentiated state.

Example 4: Human iPS Cell Culture on the Culture Plate Coated with 521E8 Plus "Another Protein"

Experimental Methods

Whether the activity of 521E8 as a cell culture matrix would be enhanced by HSA or gelatin was examined using a 24-well cell culture plate (Becton Dickinson, cat#353047; usable surface area: 1.88 cm$^2$) coated with 521E8 alone or plus HSA (Biological Industries, cat#05-720-1B) or gelatin (Nippi, Inc., APAT) according to the method described in Example 3. The specific procedure is as follows. 521E8 was diluted in PBS (Gibco, cat#10010-049, pH 7.4) containing HSA or gelatin at a final concentration of 500 µg/mL, and this 521E8 solution was added to the wells of a plate in such a volume that the coating concentration would be 0.25 µg/cm$^2$. The plate was incubated with gentle agitation at 4° C. overnight (for about 18 hours) for coating. In addition, 521E8 was serially diluted in PBS without HSA or gelatin, and a plate was similarly coated with these 521E8 solutions in such a volume that the coating concentration would be 0.5 µg/cm$^2$ or 0.25 µg/cm$^2$, as the control. After removal of the coating solution, 201B7 cells prepared by dissociation into single cells with TrypLE Select (Life Technologies, cat#A 12859-01) were seeded at 4.15×10=cells/cm$^2$ and cultured for one week. A TeSR2/NutriStem (1:1) mixed medium was used as culture medium. The culture medium was replaced every other day. After one week of culture, the cells were stained for alkaline phosphatase. The alkaline phosphatase staining was performed using a Leukocyte Alkaline Phosphatase Kit (Sigma-Aldrich, cat#86R-1KT) according to the attached recommended protocol.

Experimental Results

Figure 6:
FIG. 6 shows the results of alkaline phosphatase staining of human iPS cells cultured on a culture plate coated with laminin 521E8 plus human serum albumin or gelatin.

The cells stained for alkaline phosphatase are shown in FIG. 6. When the plate was coated with 521E8 in the absence of HSA and gelatin, a large number of colonies and sufficient growth of the iPS cells were observed on the plate coated at 0.5 µg/cm$^2$. On the plate coated at 0.25 µg/cm$^2$, the iPS cells were grown, but the growth was so limited that formed colonies were not distributed over the entire surface of the well. On the other hand, when the plate was coated with 521E8 at 0.25 µg/cm$^2$ using the coating solution containing 521E8 and 500 µg/mL HSA or gelatin, formed colonies were distributed over the entire surface of the well, and the growth of the iPS cells was significantly greater than that on the plate coated with 521E8 at 0.25 µg/cm$^2$ in the absence of HSA and gelatin. This growth of the iPS cells was comparable or superior to that on the plate coated with 521E8 alone at 0.5 µg/cm$^2$. In addition, the human iPS cells cultured on the plate coated with 521E8 plus HSA or gelatin were strongly stained for alkaline phosphatase activity, indicating that the iPS cells were maintained in an undifferentiated state.

These results show that the addition of HSA or gelatin can enhance the activity of not only laminin E8 fragment 511E8 but also 521E8. Also shown is that the addition of HSA or gelatin can halve the amount of a laminin E8 fragment used for coating a plate. The reduction of the amount of a laminin E8 fragment used for coating leads to saving the cost of iPS cell culture, which is a great merit.

Example 5: Long-Term Stabilization of 511E8-Containing Coating Solution by Addition of "Another Protein"

Whether the activity of 511E8 diluted approximately to the coating concentration in PBS (Gibco, cat#10010-049, pH 7.4) containing "another protein", such as HSA and gelatin, could be stably maintained for a long period of time was examined using integrin binding activity as an indicator.

Experimental Methods

511E8 was diluted to 32 nM (4.8 µg/mL) in PBS containing 500 µg/mL gelatin (Nippi, Inc., APAT), and the 511E8 solution was stored in a glass bottle at 4° C. Separately, 511E8 was diluted to 32 nM in gelatin-free PBS, and this 511E8 solution was stored in another glass bottle at 4° C. After 16 weeks of storage, these coating solutions were separately diluted to 22 nM, 11 nM, 5.5 nM and 0 nM, and the diluted solutions were added at 50 µL/well to a 96-well plate (Becton Dickinson, cat#353072). The plate was incubated with gentle agitation at 4° C. overnight for coating. In addition, 511E8 was freshly diluted to 22 nM, 11 nM, 5.5 nM and 0 nM in PBS immediately before coating, and a 96-well plate was similarly coated with these coating solutions at 50 µL/well as the control. Integrin binding activity was measured in the same manner as described in Example 1.

Experimental Results

Figure 7:
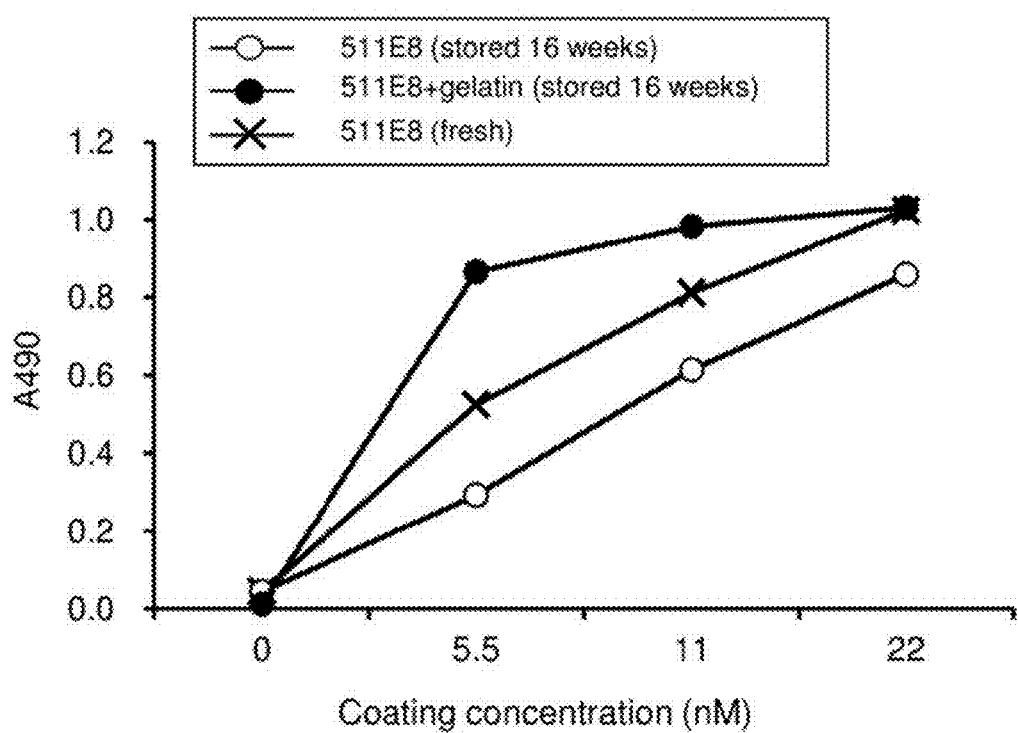
FIG. 7 shows the comparison of integrin binding activities between a coating solution of a laminin 511E8 fragment prepared immediately before use and a coating solution of the laminin 511E8 fragment plus gelatin stored in a glass bottle at 4° C. for 16 weeks.

The results are shown in FIG. 7. When the gelatin-free coating solution stored for 16 weeks at 4° C. was used, the integrin binding activity was significantly lower at every coating concentration ranging from 5.5 to 22 nM in comparison with the activity level on the plate coated with the coating solutions prepared immediately before use. On the other hand, when the coating solution which had been supplemented with 500 µg/mL of gelatin and stored for 16 weeks were used, the reduction of the integrin binding activity caused by long-term storage was not observed at a standard coating concentration of 22 nM (equivalent to 0.5 µg/cm$^2$). Surprisingly, significant increase in the integrin binding activity was observed at the coating concentrations of 5.5 nM and 11 nM. Moreover, the integrin binding activities at the coating concentrations of 5.5 nM and 11 nM were almost comparable to that at 22 nM, demonstrating that the activity-enhancing effect of gelatin on 511E8 was maintained after 16 weeks of storage at 4° C.

Example 6: Long-Term Stabilization of 521E8-Containing Coating Solution by Addition of "Another Protein"

Whether the activity of 521E8 diluted approximately to the coating concentration in PBS (Gibco, cat#10010-049, pH 7.4) containing "another protein", such as HSA and gelatin, could be stably maintained for a long period of time was examined using the growth of human iPS cells as an indicator.

Experimental Methods

521E8 was diluted to 16 nM (2.4 µg/mL) and 8 nM (1.2 µg/mL) in PBS containing 500 µg/mL or 2000 µg/mL HSA (Biological Industries, cat#05-720-1B), and the 521E8 solutions were stored in separate 50-mL polypropylene tubes (IWAKI Cat. No. 2345-050, Asahi Glass Co., Ltd.) at 4'C. Separately, 521E8 was diluted 20 to 16 nM (2.4 µg/mL) and 8 nM (1.2 µg/mL) in HSA-free PBS, and these 521E8 solutions were also stored in separate 50-mL polypropylene tubes at 4° C. After 13 weeks of storage, the 521E8-containing coating solutions were added to a 24-well cell culture plate (Becton Dickinson, cat#353047; usable surface area: 1.88 cm$^2$) in such a volume that the coating concentration would be 0.25 µg/cm$^2$ or 0.125 µg/cm$^2$. The plate was incubated with gentle agitation at 4° C. overnight for coating. In addition, 521E8 was freshly serially diluted in HSA-free PBS immediately before coating, and a plate was similarly coated with these 521E8 solutions in such a volume that the coating concentration would be 0.25 µg/cm² or 0.125 µg/cm², as the control. After removal of the coating solution, a human iPS cell line 409B2 prepared by dissociation into single cells with TrypLE Select (Life Technologies, cat#A 12859-01) was seeded at 1.3×10⁴ cells/well and cultured for 6 days. A TeSR2/NutriStem (1:1) mixed medium was used as culture medium. The culture medium was replaced every other day. After 6 days of culture, the cells were stained for alkaline phosphatase. The alkaline phosphatase staining was performed using a Leukocyte Alkaline Phosphatase Kit (Sigma-Aldrich, cat#86R-1KT) according to the attached recommended protocol.

Experimental Results

Figure 8:
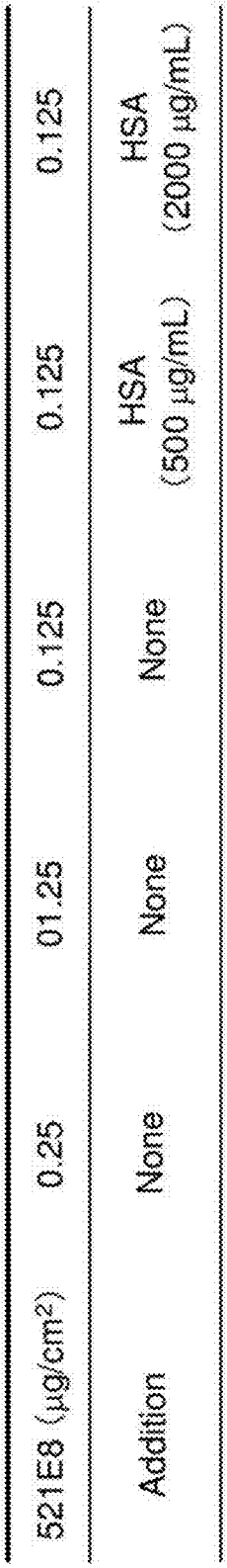
FIG. 8 shows the results of alkaline phosphatase staining of human iPS cells cultured for 6 days on a 24-well cell culture plate coated with a coating solution of laminin 521E8 plus human serum albumin stored in a polypropylene tube at 4° C. for 13 weeks or a coating solution of laminin 521E8 prepared immediately before use.

The cells stained for alkaline phosphatase are shown in FIG. 8. When the plate was coated with 521E8 in the absence of HSA, a large number of colonies and sufficient growth of the iPS cells were observed on the plate coated at 0.25 µg/cm². On the plate coated at 0.125 µg/cm², the iPS cells were grown, but the growth was so limited that formed colonies were not distributed over the entire surface of the well. Such a difference in the growth of iPS cells was observed both in the case where the coating solution was prepared immediately before use and in the case where the coating solution was prepared beforehand and kept refrigerated for 13 weeks. On the other hand, when the plate was coated with 521E8 at 0.125 µg/cm² using the coating solution which had been supplemented with 500 µg/mL or 2000 µg/mL HSA and kept refrigerated for 13 weeks, formed colonies were distributed over the entire surface of the well, and the growth of the iPS cells was significantly greater than that on the plate coated with 521E8 at the same concentration in the absence of HSA. This growth of the iPS cells was comparable to that on the plate coated with 521E8 alone at 0.25 µg/cm². In addition, the human iPS cells cultured on the plate coated with 521E8 plus HSA were strongly stained for alkaline phosphatase activity, indicating that the cells were maintained in an undifferentiated state.

Example 7: Long-Term Storage Test of 1× Coating Solution Containing 511E8 and "Another Protein"

Experimental Methods (1) Preparation and Storage of 1× Coating Solution

511E8 was diluted to 3.2 µg/mL and 1.6 µg/mL in PBS (Nacalai Tesque) containing 500 µg/mL or 2000 µg/mL HSA (Biological Industries, cat#05-720-1B), and these 511E8 solutions were stored in separate 50-mL polypropylene tubes (Becton Dickinson) at 4° C. Separately, 511E8 was diluted to 3.2 µg/mL and 1.6 µg/mL in PBS (Nacalai Tesque) containing 500 µg/mL or 2000 µg/mL gelatin (Nippi, Inc., APAT), and these 511E8 solutions were stored in separate 50-mL polypropylene tubes at 4° C. In addition, 511E8 was diluted to 3.2 µg/mL and 1.6 µg/mL in PBS without "another protein", such as HSA and gelatin, and these 511E8 solutions were also stored in separate 50-mL polypropylene tubes at 4° C. as the control.

(2) Plate Coating

After the coating solutions were kept refrigerated for 12 months, a 24-well cell culture plate (Becton Dickinson, cat#353047; usable surface area: 1.88 cm²) and a 6-well cell culture plate (Becton Dickinson, cat#353046; usable surface area: 9.6 cm²) were coated with the coating solutions. The volume of the coating solution was 300 µL/well for the 24-well plate or 1.5 mL/well for the 6-well plate, so that the coating concentration of 511E8 would be 0.5 µg/cm² (for the coating solution containing 3.2 µg/mL 511E8) or 0.25 µg/cm² (for the coating solution containing 1.6 µg/mL 511E8). After addition of the coating solutions to the wells of a plate, the plate was incubated with gentle agitation at 4° C. overnight for coating. In addition, 511E8 was freshly serially diluted in PBS without "another protein", such as HSA and gelatin, immediately before coating, and a plate was similarly coated with these 511E8 solutions in such a volume that the coating concentration would be 0.5 µg/cm² or 0.25 µg/cm², as the control.

(3) Human iPS Cell Culture

After removal of the coating solution, a human iPS cell line 409B2 prepared by dissociation into single cells with TrypLE Select (Life Technologies, cat#A 12859-01) was seeded at 1.3×10⁴ cells/well on a 24-well plate and 5.2×10⁴ cells/well on a 6-well plate, and cultured for one week. A TeSR2/NutriStem (1:1) mixed medium was used as culture medium. Only at the time of the cell seeding, a ROCK inhibitor (Y-27632, Wako Pure Chemical Industries, Ltd.) was added at a final concentration of 10 µM to the culture medium for inhibition of apoptosis. On the day following the cell seeding, the culture medium was replaced. After that, the culture medium was replaced every other day till day 5, and from then on, the culture medium was replaced daily. The cells were grown to 80 to 90% confluency after one week and then subjected to the test described below.

(4) Alkaline Phosphatase Staining

The human iPS cells cultured on the 24-well plate were subjected to alkaline phosphatase staining. The alkaline phosphatase staining was performed as described in Example 6, using a Leukocyte Alkaline Phosphatase Kit (Sigma-Aldrich, cat#86R-1KT) according to the attached recommended protocol.

(5) Flow Cytometry Analysis

The human iPS cells cultured on the 6-well plate were subjected to flow cytometry analysis. The flow cytometry analysis was performed according to a partially modified version of the method of Yamada et al. (Yamada et al., Biochem. J., 2008). For the analysis, the following antibodies against undifferentiation markers were used: FITC-labeled mouse IgG3 (control), FITC-labeled anti-mouse SSEA4 antibody, FITC-labeled anti-mouse Tra-1-60 antibody, Alexa fluor 488-labeled IgG1 (control) (those described thus far are against cell-surface markers), and Alexa fluor 488-labeled anti-OCT3/4 antibody (against an intracellular marker). These antibodies are manufactured by BD Pharmingen.

After removal of the culture medium, the iPS cells were dissociated into single cells with TrypLE Select and treated with PBS-diluted formalin (formalin:PBS=1:10) at room temperature for 10 minutes for fixation. The fixed cells were washed twice with PBS and suspended in 100 µL of PBS. The suspension was separated into an 80-µL cell suspension and a 20-µL cell suspension.

The 80-µL cell suspension was used for detection of cell-surface markers (IgG3, SSEA4, Tra-1-60 and IgG1). After centrifugation at 1500 rpm, the supernatant was removed and the residue was resuspended in 80 µL of 1.5% fetal bovine serum (FBS, Life Technologies)/PBS. This cell suspension was divided into 4 aliquots (20 µL/tube), and the tubes were allowed to stand on ice for 15 minutes for blocking. After blocking, 20 µL each of the four antibodies were added to the separate tubes, and the tubes were incubated on ice in a light-shielding condition for 1 hour.

The 20-µL cell suspension was used for detection of an intracellular marker (OCT3/4). This cell suspension was treated with the addition of 20 µL of 0.2% Triton X-100/PBS (final concentration of 0.1%) at room temperature for 15 minutes for cell permeabilization. After centrifugation, the supernatant was removed, and the residue was treated with 100 μL of 1.5% FBS/PBS at room temperature for 15 minutes for blocking. After blocking, 20 μL of anti-OCT3/4 antibody was added to the tube, and the tube was incubated at room temperature in a light-shielding condition for 1 hour.

The cells stained with each antibody were washed with PBS and resuspended in 500 μL PBS. The cells were analyzed with a flow cytometer (FACScan, manufactured by BD Co.).

Experimental Results (1) Alkaline Phosphatase Staining

Figure 9:
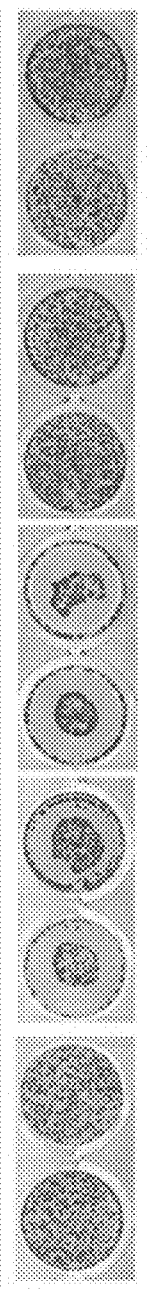
FIG. 9 shows the results of alkaline phosphatase staining of human iPS cells cultured for one week on a 24-well cell culture plate coated with a coating solution of laminin 511E8 plus human serum albumin stored in a polypropylene tube at 4° C. for 12 months or a coating solution of laminin 511E8 prepared immediately before use.

The cells stained for alkaline phosphatase are shown in FIGS. 9 and 10. FIG. 9 shows the results of the experiment in which HSA was used as "another protein", and FIG. 10 shows the results of the experiment in which gelatin was used as "another protein". When the plate was coated with 511E8 in the absence of "another protein", the iPS cells on the plate coated at 0.25 μg/cm² were grown, but the growth was so limited that formed colonies were not distributed over the entire surface of the well (see the 2nd and 3rd columns from the left in FIGS. 9 and 10). This result was common to both the case where the coating solution prepared immediately before use was used and the case where the coating solution stored for 12 months was used. When the plate was coated at 0.5 μg/cm² with the coating solution without "another protein" prepared immediately before use, sufficient growth of the iPS cells was observed (see the far-left column in FIGS. 9 and 10).

On the other hand, when the plate was coated with 511E8 at 0.25 μg/cm² using the coating solution which had been supplemented with 500 μg/mL or 2000 μg/mL HSA or gelatin and kept refrigerated for 12 months, formed colonies were distributed over the entire surface of the well, and the growth of the iPS cells was comparable to that on the plate coated with 511E8 at 0.5 μg/cm² using the coating solution prepared immediately before use, as is clear from FIGS. 9 and 10. That is, even when the 1× coating solution stored for 12 months was used, iPS cell growth comparable to that observed at the coating concentration of 511E8 recommended for human iPS cell culture (0.5 μg/cm²: Non Patent Literature 2) was achieved at half (0.25 μg/cm²) the recommended coating concentration of 511E8. In addition, the human iPS cells cultured on the plate coated with 511E8 plus HSA or gelatin were strongly stained for alkaline phosphatase activity, indicating that the iPS cells were maintained in an undifferentiated state.

(2) Flow Cytometry Analysis

Figure 11:
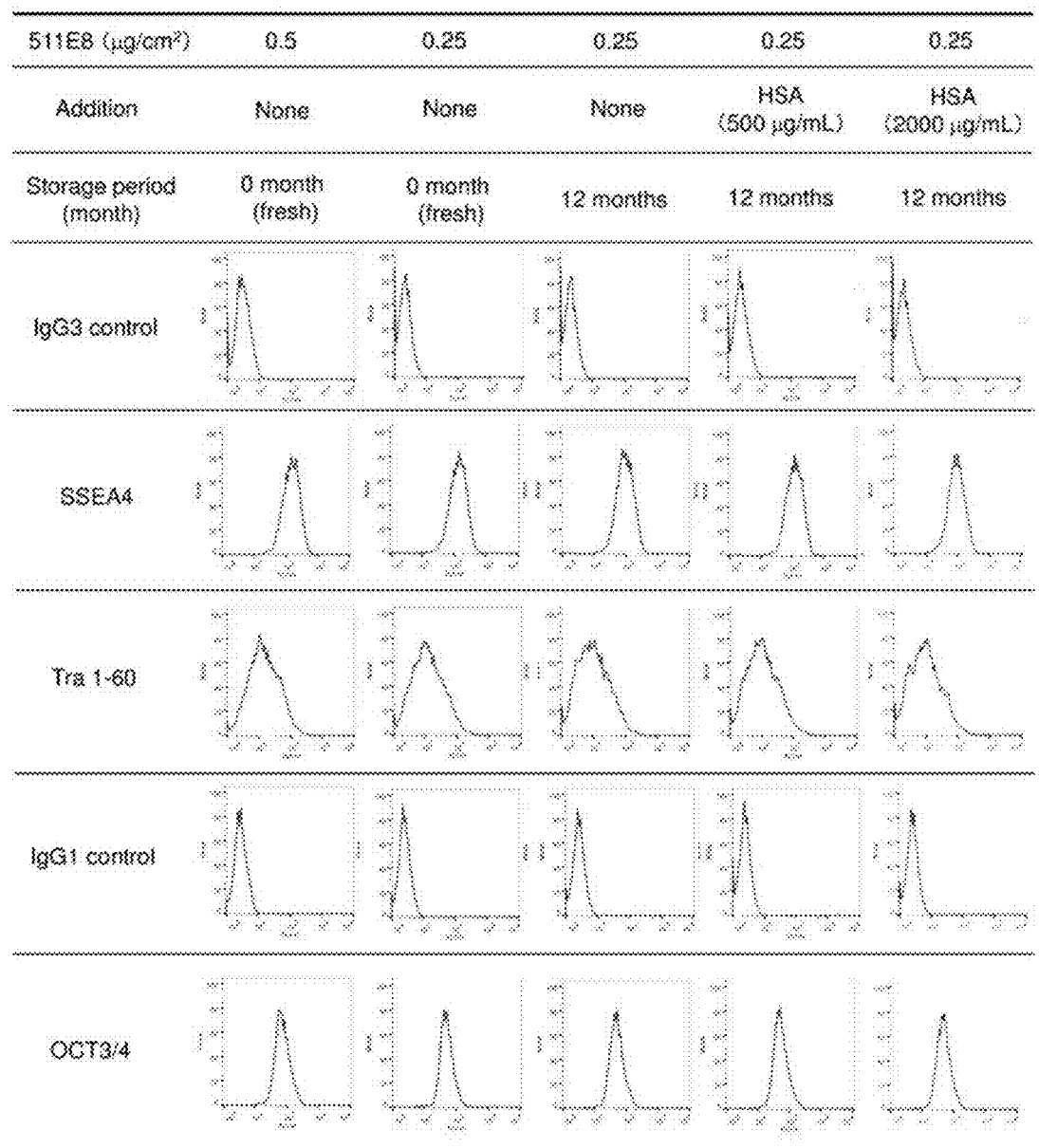
FIG. 11 shows the results of FACS analysis of human iPS cells cultured for one week on a 6-well cell culture plate coated with a coating solution of laminin 511E8 plus human serum albumin stored in a polypropylene tube at 4° C. for 12 months or a coating solution of laminin 511E8 prepared immediately before use.
Figure 12:
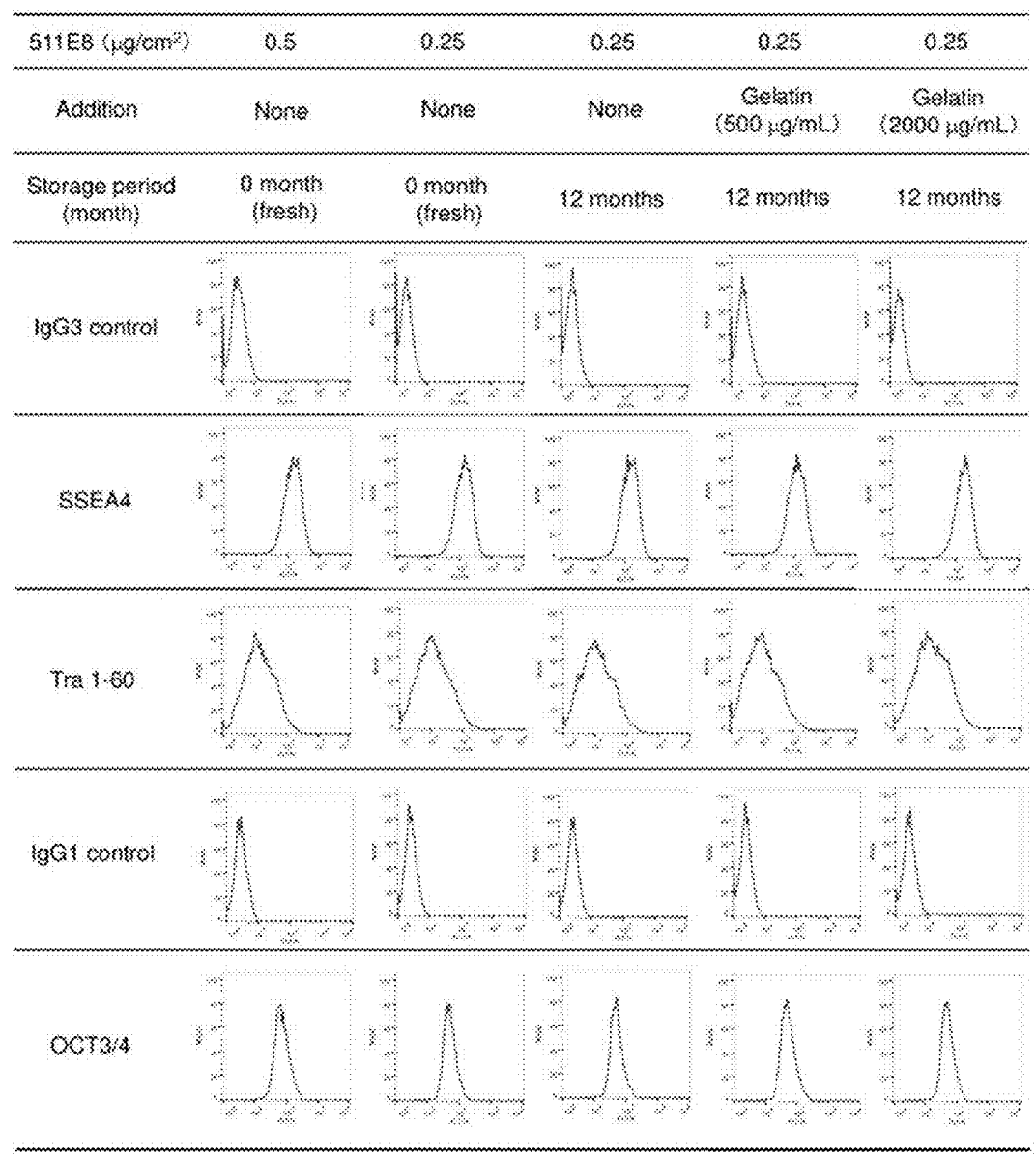
FIG. 12 shows the results of FACS analysis of human iPS cells cultured for one week on a 6-well cell culture plate coated with a coating solution of laminin 511E8 plus gelatin stored in a polypropylene tube at 4° C. for 12 months or a coating solution of laminin 511E8 prepared immediately before use.

The results are shown in FIGS. 11 and 12. FIG. 11 shows the results of the experiment in which HSA was used as "another protein", and FIG. 12 shows the results of the experiment in which gelatin was used as "another protein". The fluorescence intensities (FL-1 intensity) of the undifferentiation markers (SSEA4, Tra-1-60 and OCT3/4) were higher than that of the IgG control in all the groups, demonstrating that the iPS cells were maintained in an undifferentiated state. The intensities were not reduced by either the addition of HSA or gelatin or the 12-month storage.

Example 8: Long-Term Storage Test of 1× Coating Solution Containing 521E8 and "Another Protein"

Experimental Methods (1) Preparation and Storage of 1× Coating Solution

521E8 was diluted to 3.2 μg/mL, 1.6 μg/mL and 0.8 μg/mL in PBS (Nacalai Tesque) containing 500 μg/mL or 2000 μg/mL HSA (Biological Industries, cat#05-720-1B), and these 521E8 solutions were stored in separate 50-mL polypropylene tubes (Becton Dickinson) at 4° C. Separately, 521E8 was diluted to 3.2 μg/mL, 1.6 μg/mL and 0.8 μg/mL in PBS containing 500 μg/mL or 2000 μg/mL gelatin (Nippi, Inc., APAT), and these 521E8 solutions were stored in separate 50-mL polypropylene tubes at 4° C. In addition, 521E8 was diluted to 3.2 μg/mL, 1.6 μg/mL and 0.8 μg/mL in PBS without "another protein", such as HSA and gelatin, and these 521E8 solutions were also stored in separate 50-mL polypropylene tubes at 4° C. as the control.

(2) Plate Coating

After the coating solutions were kept refrigerated for 12 months, a 24-well cell culture plate and a 6-well cell culture plate were coated with 521E8 as described in Example 7, using the coating solutions. The coating concentration of 521E8 was 0.5 μg/cm² (for the coating solution containing 3.2 μg/mL 521E8), 0.25 μg/cm² (for the coating solution containing 1.6 μg/mL 521E8), or 0.125 μg/cm² (for the coating solution containing 0.8 μg/mL 521E8). In addition, 521E8 was freshly serially diluted in PBS without "another protein", such as HSA and gelatin, immediately before coating, and a plate was similarly coated with these 521E8 solutions in such a volume that the coating concentration would be 0.5 μg/cm², 0.25 μg/cm² or 0.125 μg/cm², as the control.

(3) Human iPS Cell Culture

Human iPS cell culture was performed in the same manner as described in Example 7.

(4) Alkaline Phosphatase Staining

Alkaline phosphatase staining was performed in the same manner as described in Example 7.

(5) FACS Analysis

FACS analysis was performed in the same manner as described in Example 7.

Experimental Results (1) Alkaline Phosphatase Staining

Figure 13:
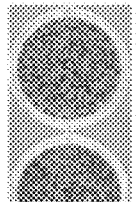
FIG. 13 shows the results of alkaline phosphatase staining of human iPS cells cultured for one week on a 24-well cell culture plate coated with a coating solution of laminin 521E8 plus human serum albumin stored in a polypropylene tube at 4° C. for 12 months or a coating solution of laminin 521E8 prepared immediately before use.
Figure 14:
FIG. 14 shows the results of alkaline phosphatase staining of human iPS cells cultured for one week on a 24-well cell culture plate coated with a coating solution of laminin 521E8 plus gelatin stored in a polypropylene tube at 4° C. for 12 months or a coating solution of laminin 521E8 prepared immediately before use.

The cells stained for alkaline phosphatase are shown in FIGS. 13 and 14. FIG. 13 shows the results of the experiment in which HSA was used as "another protein", and FIG. 14 shows the results of the experiment in which gelatin was used as "another protein". When the plate was coated with 521E8 in the absence of "another protein", the iPS cells on the plate coated at 0.125 μg/cm² were hardly grown (see the 2nd and 3rd columns from the left in FIG. 13). On the plate coated at 0.25 μg/cm², the iPS cells were grown, but the growth was so limited that formed colonies were not distributed over the entire surface of the well (see the far-left column in FIG. 13 and the 2nd and 3rd columns from the left in FIG. 14). These results were common to both the case where the coating solution prepared immediately before use was used and the case where the coating solution stored for 12 months was used. When the plate was coated at 0.5 μg/cm² with the coating solution without "another protein" prepared immediately before use, sufficient growth of the iPS cells was observed (see the far-left column in FIG. 14).

On the other hand, when the plate was coated with 521E8 at 0.125 μg/cm² using the coating solution which had been supplemented with 500 μg/mL or 2000 μg/mL HSA and kept refrigerated for 12 months, formed colonies were distributed over the entire surface of the well, and the growth of the iPS cells was remarkably greater than on the plate coated with 521E8 at 0.25 μg/cm² using the coating solution prepared immediately before use, as is clear from FIG. 13. When the plate was coated with 521E8 at 0.25 μg/cm² using the coating solution which had been supplemented with 500 μg/mL or 2000 μg/mL gelatin and kept refrigerated for 12 months, formed colonies were distributed over the entire surface of the well, and the growth of the iPS cells was comparable to that on the plate coated with 521E8 at 0.5 μg/cm² using the coating solution prepared immediately before use, as is clear from FIG. 14. That is, even when the 1× coating solution stored for 12 months was used at a 521E8 coating concentration of one-fourth to half (0.125 to 0.25 μg/cm²) of 0.5 μg/cm², sufficient growth of the iPS cells was achieved as in the case where the coating solution without "another protein" prepared immediately before use was used at a 521E8 coating concentration of 0.5 μg/cm². In addition, the human iPS cells cultured on the plate coated with 521E8 plus HSA or gelatin were strongly stained for alkaline phosphatase activity, indicating that the iPS cells were maintained in an undifferentiated state.

(2) Flow Cytometry Analysis

Figure 15:
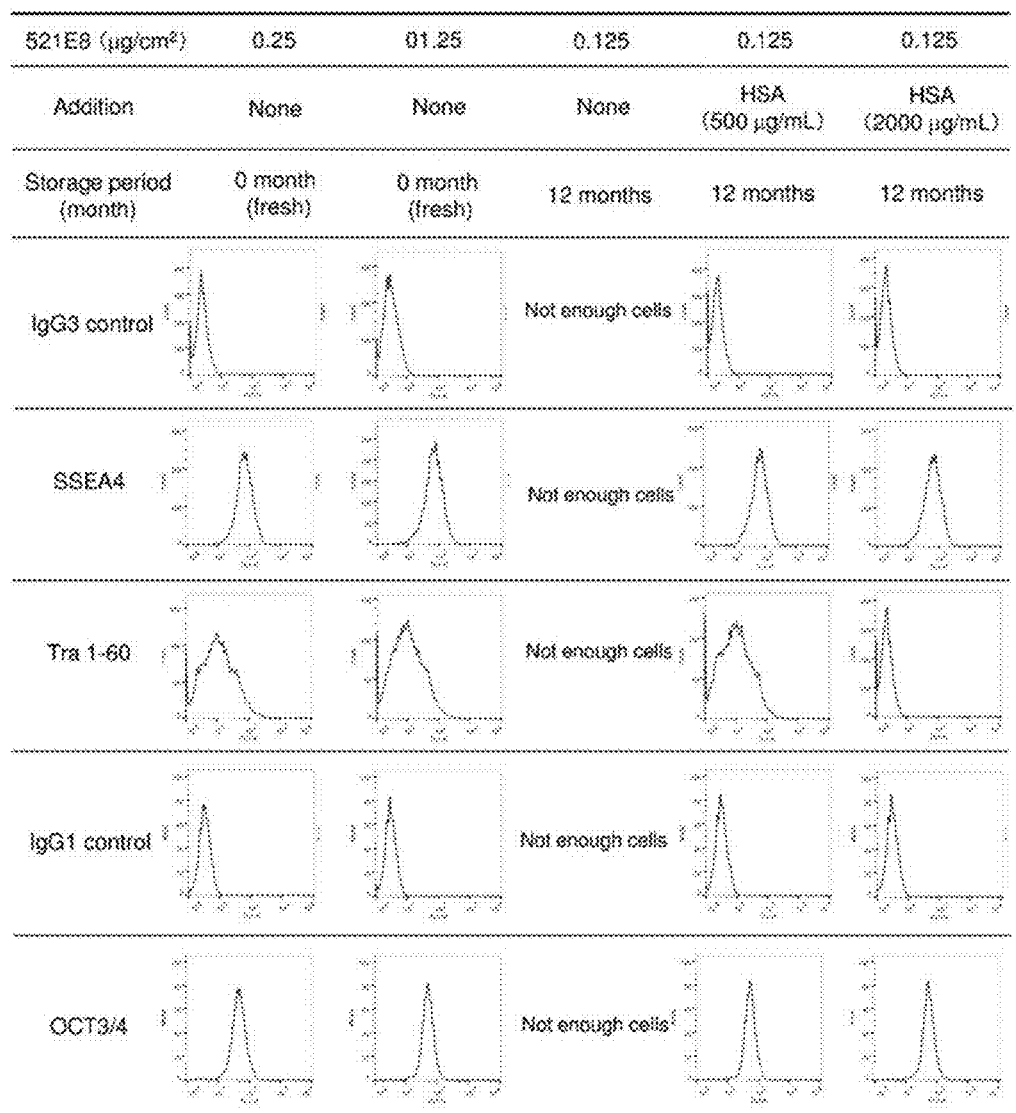
FIG. 15 shows the results of FACS analysis of human iPS cells cultured for one week on a 6-well cell culture plate coated with a coating solution of laminin 521E8 plus human serum albumin stored in a polypropylene tube at 4° C. for 12 months or a coating solution of laminin 521E8 prepared immediately before use.
Figure 16:
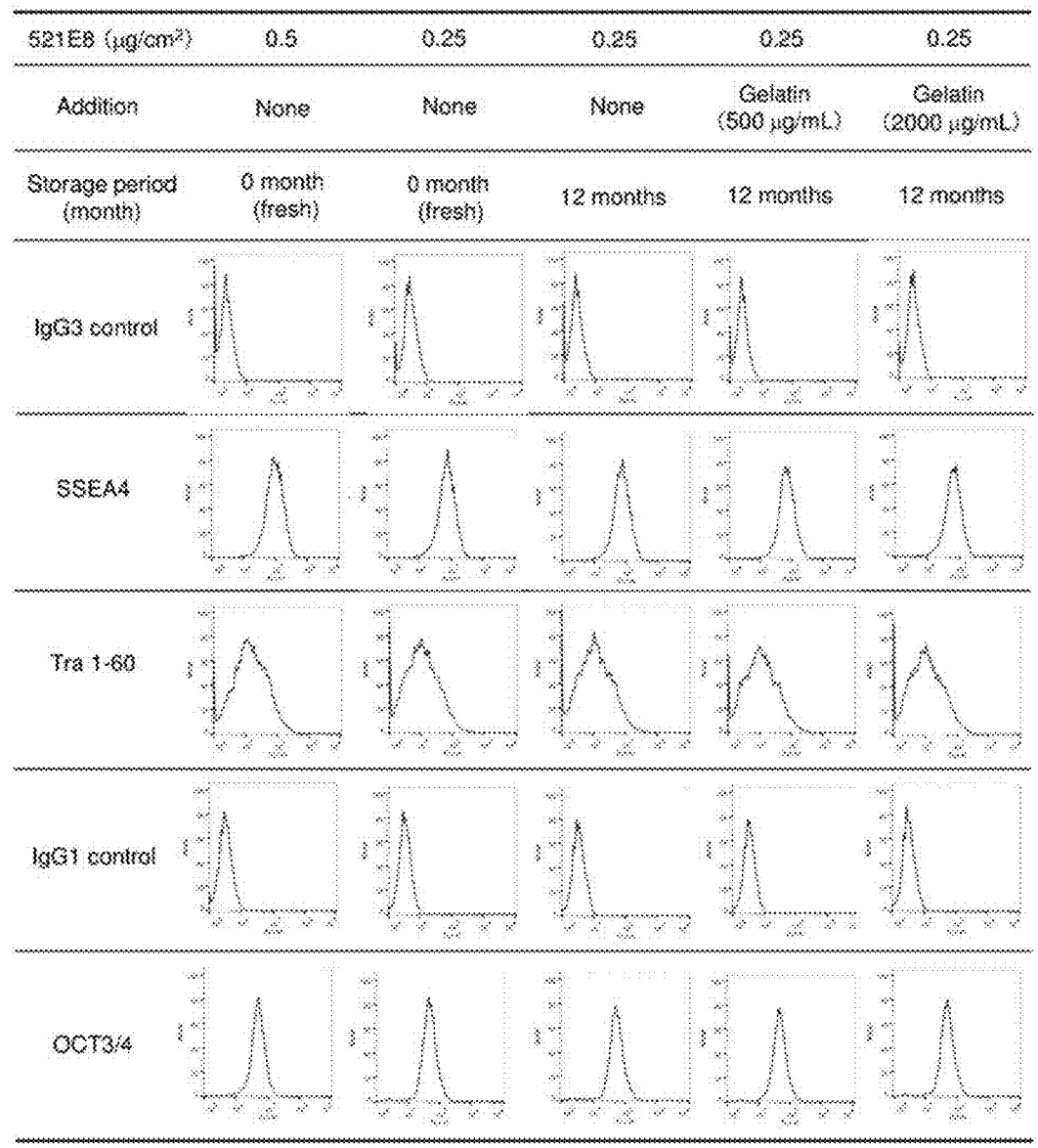
FIG. 16 shows the results of FACS analysis of human iPS cells cultured for one week on a 6-well cell culture plate coated with a coating solution of laminin 521E8 plus gelatin stored in a polypropylene tube at 4° C. for 12 months or a coating solution of laminin 521E8 prepared immediately before use.

The results are shown in FIGS. 15 and 16. FIG. 15 shows the results of the experiment in which HSA was used as "another protein", and FIG. 16 shows the results of the experiment in which gelatin was used as "another protein". The fluorescence intensities (FL-1 intensity) of the undifferentiation markers (SSEA4, Tra-1-60 and OCT3/4) were higher than that of the IgG control in all the groups, demonstrating that the iPS cells were maintained in an undifferentiated state. The intensities were not reduced by either the addition of HSA or the 12-month storage. For the group in which the plate was coated with 521E8 at 0.125 μg/cm² using the coating solution without "another protein" stored for 12 months, FACS analysis was impossible to carry out because the cell number was not sufficient for the analysis.

The above results, taken together, show that the addition of "another protein" such as HSA and gelatin can enhance the activity of laminin E8 as a cell culture matrix even when the laminin E8 is diluted to a ready-to-use concentration, and furthermore, allows a 1× coating solution of the laminin E8 to be kept refrigerated in a stable condition for a long period of time, for example, one year or longer. Also shown is that the addition of "another protein" such as HSA and gelatin causes no adverse effect on the maintenance of human pluripotent stem cells in an undifferentiated state.

A freeze-dried product of 511E8 for coating culture vessels is commercially available (trade name: iMatrix-511, manufactured by Nippi, Inc.). In a recommended procedure for use as a culture matrix for human pluripotent stem cells, this freeze-dried laminin 511E8 product is dissolved at a concentration of 200 to 1000 μg/mL, and this solution is aliquoted and kept frozen as a 511E8 stock solution until use. For coating a culture plate, for example, the frozen stock solution is thawed and diluted to 3 to 5 μg/mL in PBS or the like, and the diluted solution is added to each well in such a volume that the coating concentration is 0.5 μg/cm². That is, thawing and dilution of the stock solution are necessary every time for coating a culture plate. According to the present invention, due to the addition of a protein such as HSA and gelatin, a 511E8 solution previously diluted to a desired coating concentration can be stably stored without loss of its activity at 4° C. for a long period of time. Accordingly, the burden on cell culture operators can be reduced, and furthermore, human errors which may occur during the preparation of coating solutions can be avoided. Another advantage is saving of the amount of 511E8 used for coating.

Example 9: Enhancement of Integrin Binding Activities of 211E8 and 411E8 by "Another Protein"

Whether the integrin binding activities of laminin E8 fragments other than 511E8 or 521E8 would be increased by the addition of HSA or gelatin was examined using 211E8 and 411E8.

Experimental Methods (1) Plate Coating

211E8 or 411E8 was serially diluted to final concentrations of 25 nM, 10 nM, 5 nM and 0 nM in PBS (Gibco, cat#10010-049, pH 7.4) containing 500 μg/mL human serum albumin (Biological Industries, cat#05-720-1B; hereinafter referred to as HSA). The diluted solutions were added at 50 L/well to a 96-well plate (Becton Dickinson, #353072, usable surface area: 0.32 cm²/well). The plate was incubated with gentle agitation at 4° C. overnight for coating.

(2) Integrin Binding Assay

Integrin binding activity was measured according to the method described in Example 1, except for using an α6β1 integrin solution (30 nM α6β1 integrin, 19.6 mM Tris, 127 mM NaCl, 0.0056% Tween-20, 0.1% BSA, 1 mM MnCl₂) for the 411E8-coated plate and using an α7X2β1 integrin solution (30 nM α7X2β1 integrin, 19.6 mM Tris, 127 mM NaCl, 0.0056% Tween-20, 0.1% BSA, 1 mM MnCl₂) for the 211E8-coated plate. The recombinant α7X2β1 integrin used for the assay was prepared according to the method of Taniguchi et al. (Yukimasa Taniguchi, Hiroyuki Ido, Noriko Sanzen Maria Hayashi, Ryoko Sato-Nishiguti, Sugiko Futaki, and Kiyotoshi Sekiguchi, "The C-terminal region of laminin β chains modulates the integrin binding affinities of laminins" The Journal of Biological Chemistry, 284, 7820-7831, 2009).

Experimental Results

Figure 17:
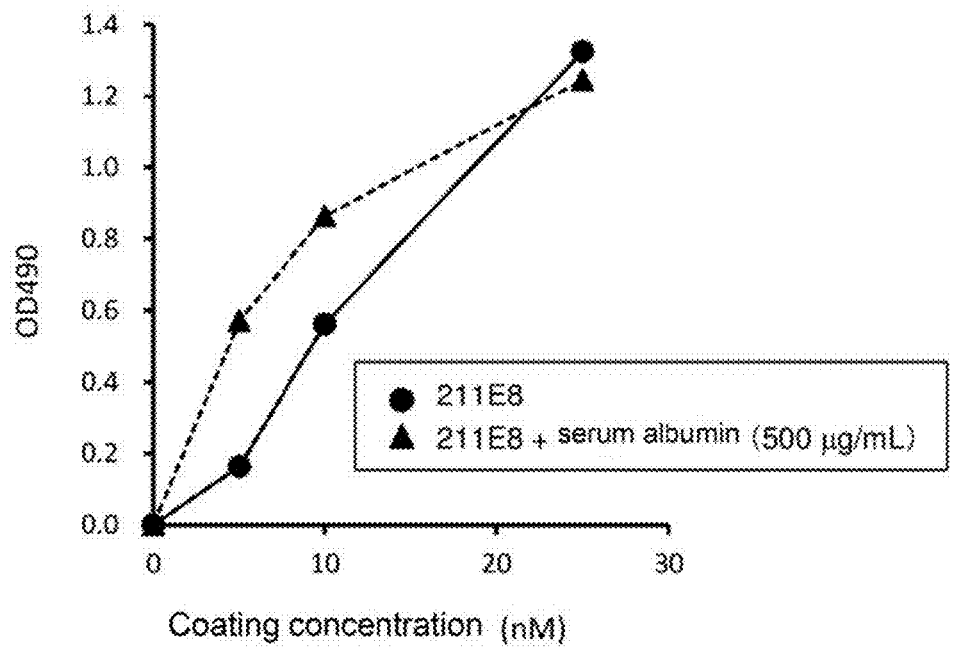
FIG. 17 shows the results of the evaluation of human serum albumin for the effect of enhancing integrin binding activity of laminin 211E8.

The results of the measurement of the integrin binding activity on the plate coated with 211E8 plus 500 μg/mL HSA are shown in FIG. 17. Significant increase in the integrin binding activity by the addition of HSA was observed when the coating concentration of 211E8 was low (5 nM and 10 nM), as with the cases of 511E8 and 521E8. Such an increase in the integrin binding activity was not observed when the coating concentration of 211E8 was 25 nM, as with the case of 521E8.

Figure 18:
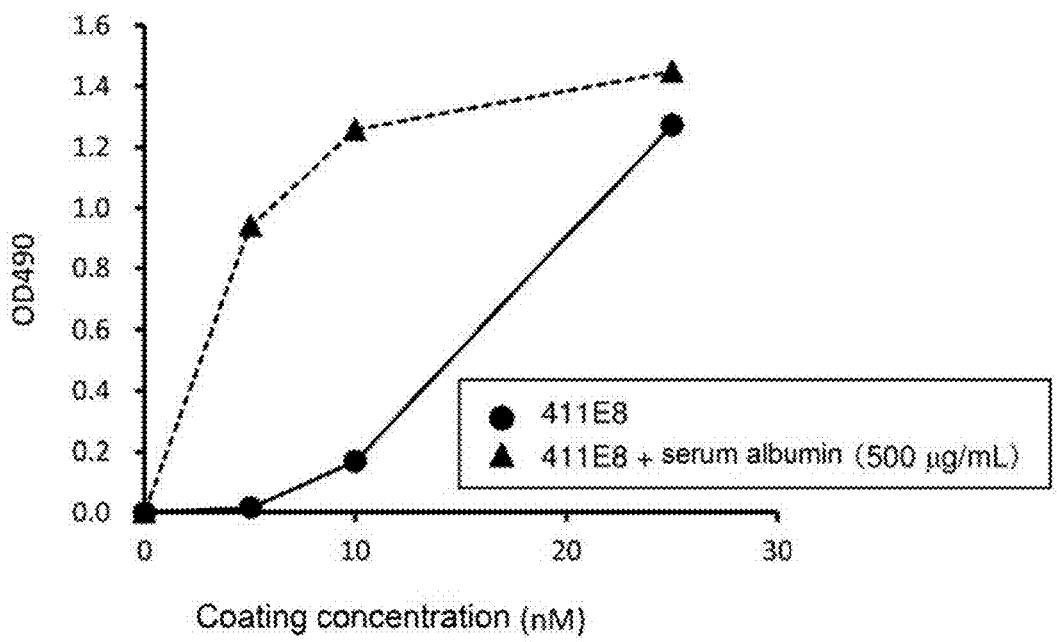
FIG. 18 shows the results of the evaluation of human serum albumin for the effect of enhancing integrin binding activity of laminin 411E8.

The results of the measurement of the integrin binding activity on the plate coated with 411E8 plus 500 μg/mL HSA are shown in FIG. 18. The increase in the integrin binding activity by the addition of HSA was more remarkably observed on the 411E8-coated plate. As shown in FIG. 18, when the coating concentration of 411E8 was low (5 nM and 10 nM), the integrin binding activity of 411E8 in the absence of HSA was only weakly detected, but the integrin binding activity of 411E8 in the presence of 500 μg/mL HSA was very strongly detected. Such remarkable enhancement of the integrin binding activity by HSA was not observed when the coating concentration of 411E8 was 25 nM.

Example 10: Enhancement of Integrin Binding Activity of Laminin Fragment Variants by "Another Protein"

Whether the integrin binding activity of a chimeric molecule composed of a laminin E8 fragment and a cell adhesion molecule or a growth factor binding molecule would be increased by addition of HSA or gelatin was examined using chimeric molecules composed of a growth factor binding molecule and 511E8. The chimeric molecules composed of a growth factor binding molecule and 511E8 were the following two kinds of 511E8 variants: a laminin fragment variant in which the domains I to III of human perlecan were fused to the N-terminal region of 511E8 (Plus#3 laminin ES) and a laminin fragment variant in which the domain I of human perlecan was fused to the C-terminal region of 511E8 (Plus#5 laminin E8). The Plus#3 laminin E8 and the Plus#5 laminin E8 were prepared by the method described in WO 2014/199754 and subjected to the measurement of the integrin binding activity.

Experimental Methods (1) Plate Coating

The Plus#3 laminin E8 or the Plus#5 laminin E8 was serially diluted to final concentrations of 22 nM, 11 nM, 5.5 nM and 0 nM in PBS (Gibco, cat#10010-049, pH 7.4) containing 500 μg/mL human serum albumin (Biological Industries, cat#05-720-1B; hereinafter referred to as HSA). The diluted solutions were added at 50 μL/well to a 96-well plate (Becton Dickinson, #353072, usable surface area: 0.32 cm$^2$/well). The plate was incubated with gentle agitation at 4° C. overnight for coating.

(2) Integrin Binding Assay

Integrin binding activity was measured using an α6β1 integrin solution (10 nM α6β1 integrin, 19.6 mM Tris, 127 mM NaCl, 0.0056% Tween-20, 0.1% BSA, 1 mM MnCl$_2$) according to the method described in Example 1.

Experimental Results

Figure 19:
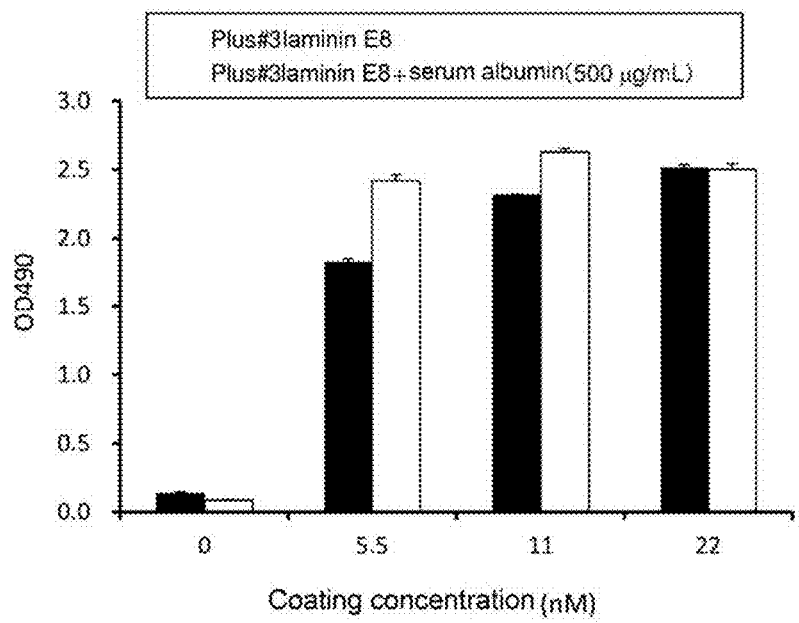
FIG. 19 shows the results of the evaluation of human serum albumin for the effect of enhancing integrin binding activity of a laminin fragment variant (in which the domains I to III of perlecan are conjugated to the N-terminal region of laminin 511E8).
Figure 20:
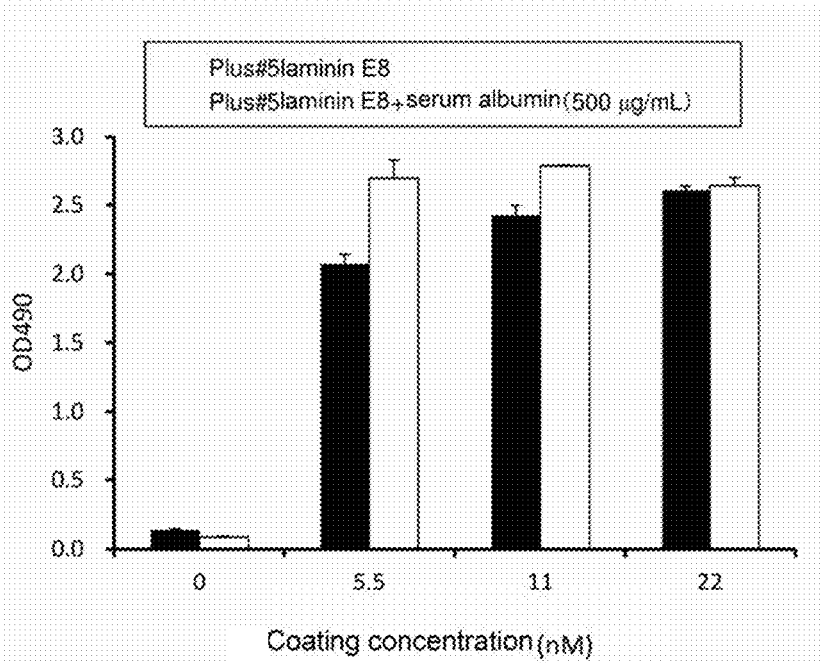
FIG. 20 shows the results of the evaluation of human serum albumin for the effect of enhancing integrin binding activity of a laminin fragment variant (in which the domain I of perlecan is conjugated to the C-terminal region of laminin 511E8).

The results of the measurement of the integrin binding activity on the plate coated with the Plus#3 laminin E8 or the Plus#5 laminin E8 plus 500 μg/mL HSA are shown in FIGS. 19 and 20. The integrin binding activity was significantly increased by the addition of 500 μg/mL HSA when the coating concentrations were 5.5 nM and 11 nM regardless of the kind of the laminin fragment variant. In contrast, when the coating concentration of the laminin fragment variant was 22 nM, the integrin binding activity was not increased by the addition of 500 μg/mL HSA.

The above results show that the addition of "another protein" such as HSA and gelatin at a high concentration can enhance the activity of not only laminin E8 fragments such as 511E8, 521E8, 211E8 and 411E8, but also chimeric molecules composed of a growth regulatory molecule (cell adhesion molecules and growth factor binding molecules) and a laminin E8 fragment. That is, the activity-enhancing method of the present invention for laminin fragments is widely applicable to laminin fragments and variants thereof (including chimeric molecules composed of a growth regulatory molecule and a laminin fragment).

The present invention is not limited to particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A method for enhancing an activity for mammalian cultured cells of a laminin fragment or a variant thereof each having integrin binding activity, the method comprising bringing a culture surface of a cell culture vessel into contact with a coating solution containing the laminin fragment or a variant thereof and a protein that is neither a laminin nor a laminin fragment, thereby achieving coating of the culture surface with the laminin fragment or a variant thereof, the coating solution containing the laminin fragment or a variant thereof at a concentration of 5 μg/mL or lower, the protein that is neither a laminin nor a laminin fragment being present at a concentration which is 100-fold or more that of the laminin fragment or a variant thereof and is 500 μg/mL or higher in the coating solution, the protein that is neither a laminin nor a laminin fragment is gelatin or serum albumin, wherein the laminin fragment is a laminin E8 fragment, wherein the variant is a chimeric molecule in which the laminin E8 fragment is conjugated with a cell adhesion molecule or a growth factor binding molecule, and the activity for mammalian cultured cells being at least one kind selected from activity for binding to cell-surface adhesion receptors, cell-adhesive activity, cell growth-supporting activity and colony formation-promoting activity.

2. The method according to claim 1, wherein the laminin fragment is derived from at least one kind selected from laminin α5β1γ1, laminin α5β2γ1, laminin α4β1γ1 and laminin α2β1γ1.

3. A method for culturing mammalian cells using a cell culture vessel coated with a laminin fragment or a variant thereof each having integrin binding activity, the cell culture vessel being prepared by bringing a culture surface of the cell culture vessel into contact with a coating solution containing the laminin fragment or a variant thereof and a protein that is neither a laminin nor a laminin fragment, the coating solution containing the laminin fragment or a variant thereof at a concentration of 5 μg/mL or lower, the protein that is neither a laminin nor a laminin fragment being present at a concentration which is 100-fold or more that of the laminin fragment or a variant thereof and is 500 μg/mL or higher in the coating solution, the protein that is neither a laminin nor a laminin fragment is gelatin or serum albumin, wherein the laminin fragment is a laminin E8 fragment, and wherein the variant is a chimeric molecule in which the laminin E8 fragment is conjugated with a cell adhesion molecule or a growth factor binding molecule.

4. The method according to claim 3, wherein the laminin fragment is derived from at least one kind selected from laminin α5β1γ1, laminin α5β2γ1, laminin α4β1γ1 and laminin α2β1γ1.

5. A solution for coating a culture surface of a cell culture vessel with a laminin fragment or a variant thereof, the solution containing a laminin fragment or a variant thereof each having an integrin binding activity and a protein that is neither a laminin nor a laminin fragment, the laminin fragment or a variant thereof being present at a concentration of 5 μg/mL or lower, the protein that is neither a laminin nor a laminin fragment being present at a concentration which is 100-fold or more that of the laminin fragment or a variant thereof and is 500 μg/mL or higher, the protein that is neither a laminin nor a laminin fragment is gelatin or serum albumin, wherein the laminin fragment is a laminin E8 fragment, and wherein the variant is a chimeric molecule in which the laminin E8 fragment is conjugated with a cell adhesion molecule or a growth factor binding molecule.

6. The solution according to claim 5, wherein the laminin fragment or a variant thereof is present in an amount adjusted so that the culture surface of the cell culture vessel is coated with the laminin fragment or a variant thereof at a concentration lower than 0.5 μg/cm$^2$.

* * * * *

SEQUENCE LISTING

```
<160> NUMBER OF SEQ ID NOS: 11

<210> SEQ ID NO 1
<211> LENGTH: 26
<212> TYPE: DNA
<213> ORGANISM: Artificial Sequence
<220> FEATURE:
<223> OTHER INFORMATION: Primer

<400> SEQUENCE: 1
atgatgatga agcttatcga taccgt                                          26

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
catcatcatg atatcgaatt cctgca                                          26

<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3
atcatatgga taaagcttat cgataccgt                                       29

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
```
gtgccagatt atgcagatat cgaattcct                                      29

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
atccttgtaa tcaagcttat cgataccgt                                      29

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
gctgccgagg atgctgctgg ccagg                                          25

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
ctaggcagga tgccgggcgg gctga                                          25

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
cttcagcata gtgctgctga cattg                                          25

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
ttacaagcat gtgctataca cagcaac                                        27

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10

```
aatgacattc tcaacaacct gaaag                                          25

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
ctagggcttt tcaatggacg gggtg                                          25
```